US011540846B2

(12) United States Patent
Rettew et al.

(10) Patent No.: US 11,540,846 B2
(45) Date of Patent: Jan. 3, 2023

(54) AIMING DEVICE FOR INTRAMEDULLARY NAILS, AND RELATED SYSTEMS AND METHODS

(71) Applicant: DEPUY SYNTHES PRODUCTS, INC., Raynham, MA (US)

(72) Inventors: Stephen R. Rettew, Downingtown, PA (US); René Haag, Berwyn, PA (US); Abhishek Ekbote, Conshohocken, PA (US); Muruganandam Mani, Downingtown, PA (US); Harry T. Hall, IV, Chester Springs, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 475 days.

(21) Appl. No.: 16/659,790

(22) Filed: Oct. 22, 2019

(65) Prior Publication Data

US 2021/0113219 A1 Apr. 22, 2021

(51) Int. Cl.
*A61B 17/17* (2006.01)
*A61B 17/16* (2006.01)

(52) U.S. Cl.
CPC ........ *A61B 17/1717* (2013.01); *A61B 17/164* (2013.01); *A61B 17/1739* (2013.01)

(58) Field of Classification Search
CPC .............. A61B 17/164; A61B 17/1717; A61B 17/1739; A61B 17/1725
See application file for complete search history.

(56) References Cited

U.S. PATENT DOCUMENTS

| | | | |
|---|---|---|---|
| 6,656,189 | B1 | 12/2003 | Wilson et al. |
| 7,175,631 | B2 | 2/2007 | Wilson et al. |
| 8,663,224 | B2 | 3/2014 | Overes et al. |
| 9,192,398 | B2 | 11/2015 | Siravo et al. |
| 9,241,744 | B2 | 1/2016 | Blake et al. |
| 9,820,760 | B2 | 11/2017 | Purohit |
| 10,307,197 | B2 | 6/2019 | Hedgeland et al. |
| 2002/0058948 | A1 | 5/2002 | Arlettaz |
| 2004/0167533 | A1 | 8/2004 | Wilson et al. |
| 2007/0083213 | A1 | 4/2007 | Siravo et al. |
| 2012/0226326 | A1 | 9/2012 | Overes et al. |
| 2013/0046311 | A1 | 2/2013 | Blake et al. |
| 2014/0188113 | A1 | 7/2014 | Overes et al. |

(Continued)

*Primary Examiner* — Samuel S Hanna
(74) *Attorney, Agent, or Firm* — BakerHostetler

(57) ABSTRACT

A device for implanting an intramedullary nail includes a base member and an adjustable member coupled together and translatable relative to each other along a direction. The device includes an insertion handle configured to carry the nail and mount to the adjustable member. A drill guide is attachable to the base member and configured to carry one or more guide sleeves for alignment with locking holes of the intramedullary nail. A first reference member extends from the base or adjustable member and has a first contact portion configured to contact an exterior location of a patient's limb. A second reference member extends from the other of the base and adjustable members and has a second contact portion configured to contact another exterior location of the limb. At least one of the first and second reference members is positionally adjustable relative to the base or adjustable member from which it extends.

9 Claims, 14 Drawing Sheets

(56) References Cited

U.S. PATENT DOCUMENTS

| | | | | |
|---|---|---|---|---|
| 2014/0249536 | A1* | 9/2014 | Jajeh | A61B 17/72 606/96 |
| 2015/0305791 | A1 | 10/2015 | Purohit | |
| 2018/0078292 | A1 | 3/2018 | Hedgeland et al. | |
| 2018/0078294 | A1 | 3/2018 | Hedgeland et al. | |
| 2018/0140310 | A1 | 5/2018 | Machamer et al. | |
| 2019/0038326 | A1 | 2/2019 | Hedgeland et al. | |
| 2019/0175240 | A1 | 6/2019 | Hedgeland et al. | |

* cited by examiner 2
4
4a
4b
5
6
8
10
12
14a
14b
15
16
18
20
21
22
23
24
25
26
26a
27
28
28a
28b
28c
29
30
30a
30b
32
34
36
40
41
42
43
44
45
47
49
A0
SP,P1
TP
CP
L
A
T P
L
A
D
72
18
30
26b
24,70
52
62
22,50
15,P1
L1A
55
100
28
60
80
64
74
58
56
32
36
54
34

78
24,70
76
L2
70a
15,P1
52
L1B
74
52
80
22,50
50a
60
32a
32
36
54

42
42
20
214
6
215
4
40
14b
44
47,49
42
242
240

AIMING DEVICE FOR INTRAMEDULLARY NAILS, AND RELATED SYSTEMS AND METHODS

TECHNICAL FIELD

The present invention relates to devices for aiming and guiding anchor members for insertion within locking holes of an intramedullary nail disposed within a medullary canal of a bone of a patient.

BACKGROUND

Surgical implants can include mechanisms that require external manipulation during or after implantation. For example, an implant can include anchoring elements, locking elements, position-adjusting elements, or other types of elements or features that allow the implant to operate in a manner to promote healing and/or stabilization of the anatomy of the patient. One example of such an implant includes an intramedullary nail implanted within a medullary cavity of a long bone, such as a femur, for example, to stabilize a fracture in the bone. It has been common practice to affix the intramedullary nail with respect to the bone by placing locking members, such as screws, through access holes drilled through at least a cortex of the bone and in alignment with locking holes, such as threaded bores, that are pre-drilled transversely in the nail. The procedure presents technical difficulties, as the pre-drilled bores in the intramedullary nail are not generally visible to the surgeon, and are difficult to localize and to align with surgical drills and placement instruments for drilling the access holes in the bone and/or inserting the locking members.

Distal targeting systems are used in many instances to detect the location of various elements of an implant during a surgical procedure. With respect to the foregoing intramedullary nail example, a distal targeting system can be employed with the surgical drill to locate the position of the one or more locking holes in the intramedullary nail and provide feedback to the physician indicating the relative positions of the locking holes with respect to a distal end of a drill bit of the surgical drill. Such distal targeting systems commonly employ radioscopy to obtain a visual image of the implanted intramedullary nail and the locking holes thereof. However, in certain medical environments, such as those in the field (e.g., search and rescue, remote ambulatory environments, and battlefields) and/or in health care facilities of developing nations (i.e., "third world" nations), radioscopy might not be available for targeting and guiding insertion of the locking members within the locking holes of the intramedullary nail.

SUMMARY

According to an embodiment of the present disclosure, a device for guiding implantation of an intramedullary nail includes a guide frame including a base frame member and an adjustable frame member coupled to the base frame member. The adjustable frame member is configured to translate relative to the base frame member along a longitudinal direction. The device includes an insertion handle configured to carry the intramedullary nail and configured to mount to the adjustable frame member. A drill guide is attachable to the base frame member and is configured to carry one or more guide sleeves for alignment with locking holes extending through the intramedullary nail. The device includes a first reference member and a second reference member. The first reference member extends from one of the base frame member and the adjustable frame member and has a first contact portion configured to contact a select exterior location of a limb of a patient. The second reference member extends from the other of the base frame member and the adjustable frame member and has a second contact portion configured to contact a second select exterior location of the limb. At least one of the first and second reference members is configured such that a relative position between its contact portion and the base or adjustable frame member from which it extends is adjustable.

According to another embodiment of the present disclosure, a method of preparing an injured limb of a patient to receive an intramedullary nail includes adapting a guide frame for engagement with a first limb of the patient. The first limb is contralateral to the injured limb. Adapting the guide frame includes contacting a first reference member that extends from an upper frame member of the guide frame against a first select exterior location of the first limb, translating the upper frame member and a lower frame member of the guide frame relative to each other along a longitudinal axis thereby adjusting a longitudinal length of the guide frame, and contacting a second reference member that extends from the lower frame member against a second select exterior location of the first limb. The method includes re-configurating the guide frame for engagement with the injured limb. The re-configuring step includes repositioning the second reference member on the lower frame member symmetrically about a reference plane that is defined by the guide frame and is coextensive with the longitudinal axis and with a transverse direction perpendicular to the longitudinal axis. The re-configuring step also includes contacting the first contact portion against a first select exterior location of the injured limb and contacting the second contact portion against a second select exterior location of the injured limb, such that the first and second select exterior locations of the injured limb are substantial contralateral counterparts of the first and second select exterior locations, respectively, of the first limb.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

Figure 1:
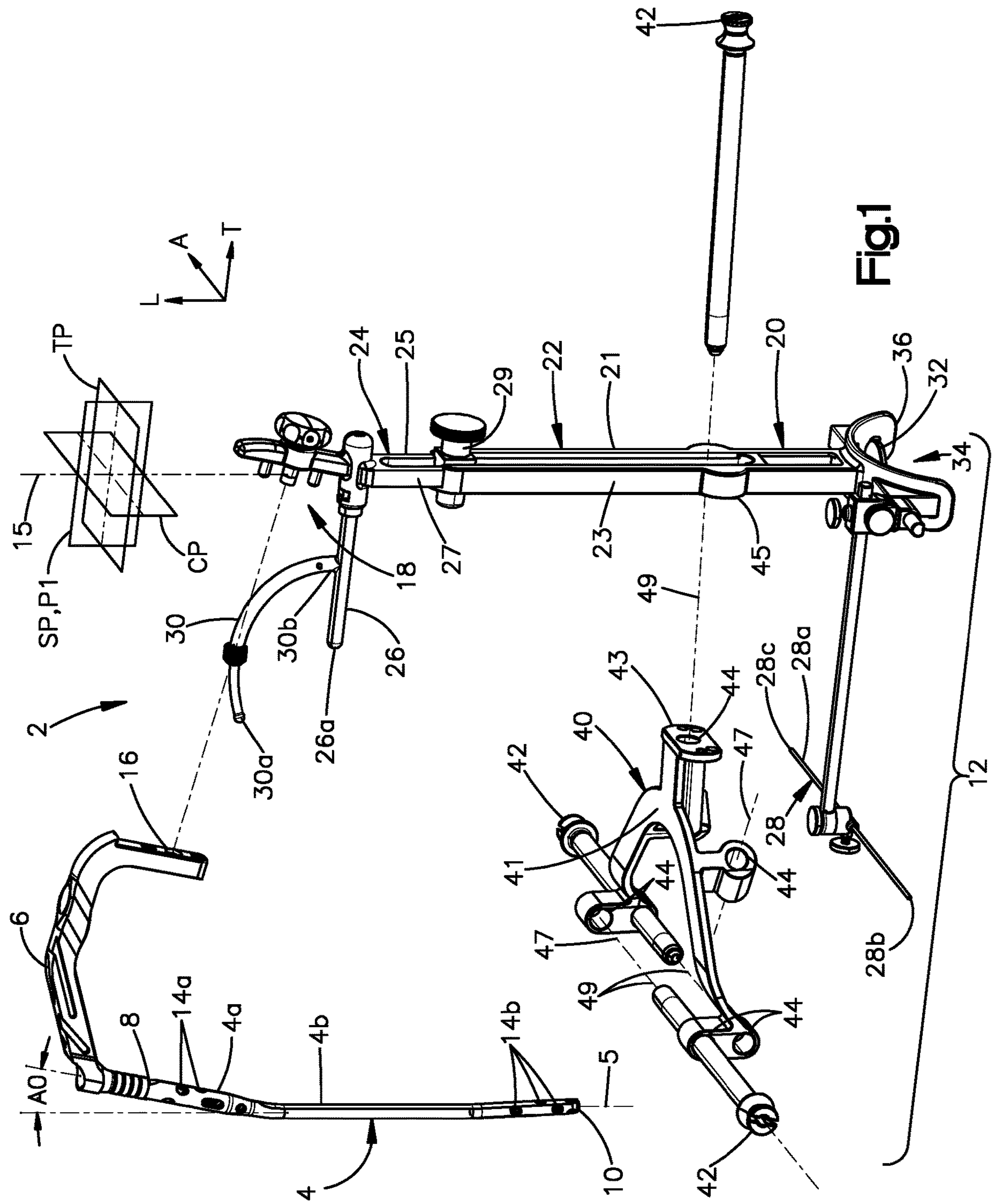
FIG. 1 is a partially exploded perspective view of a system for implanting an intramedullary nail, the system including an aiming device having a targeting guide member for targeting distal locking holes of the intramedullary nail, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The embodiments described below pertain to aiming guides for an intramedullary nail, particularly aiming guides for assessing physiological parameters, such as the length, width, and/or rotation or articulation (i.e., flexion/extension)) of a portion of a patient's limb in need of surgical repair, such as the lower leg for repairing the tibia and/or fibula, the upper leg for repairing the femur, the upper arm for repairing the humerus, and/or the lower arm for repairing the radius and/or ulna. The aiming guides are configured to first engaging with the corresponding portion of the opposite healthy or "good" limb and determining the physiological parameters of the good limb. In this manner, the aiming guides of the present disclosure employ the good limb as a template for the physiological parameters of the limb in need of surgical repair. In this manner, the aiming devices of the present disclosure also preferably employ the good limb as a template for targeting and aiming distal locking members through the intramedullary nail inserted within the intramedullary canal of the limb in need of surgical repair. The good limb is also referred to herein as the "template limb", and the limb in need of surgical repair is also referred to herein as the "implant limb." The aiming guides of the present disclosure are particularly useful in medical environments where radioscopy and/or fluoroscopy are not available.

Figure 2:
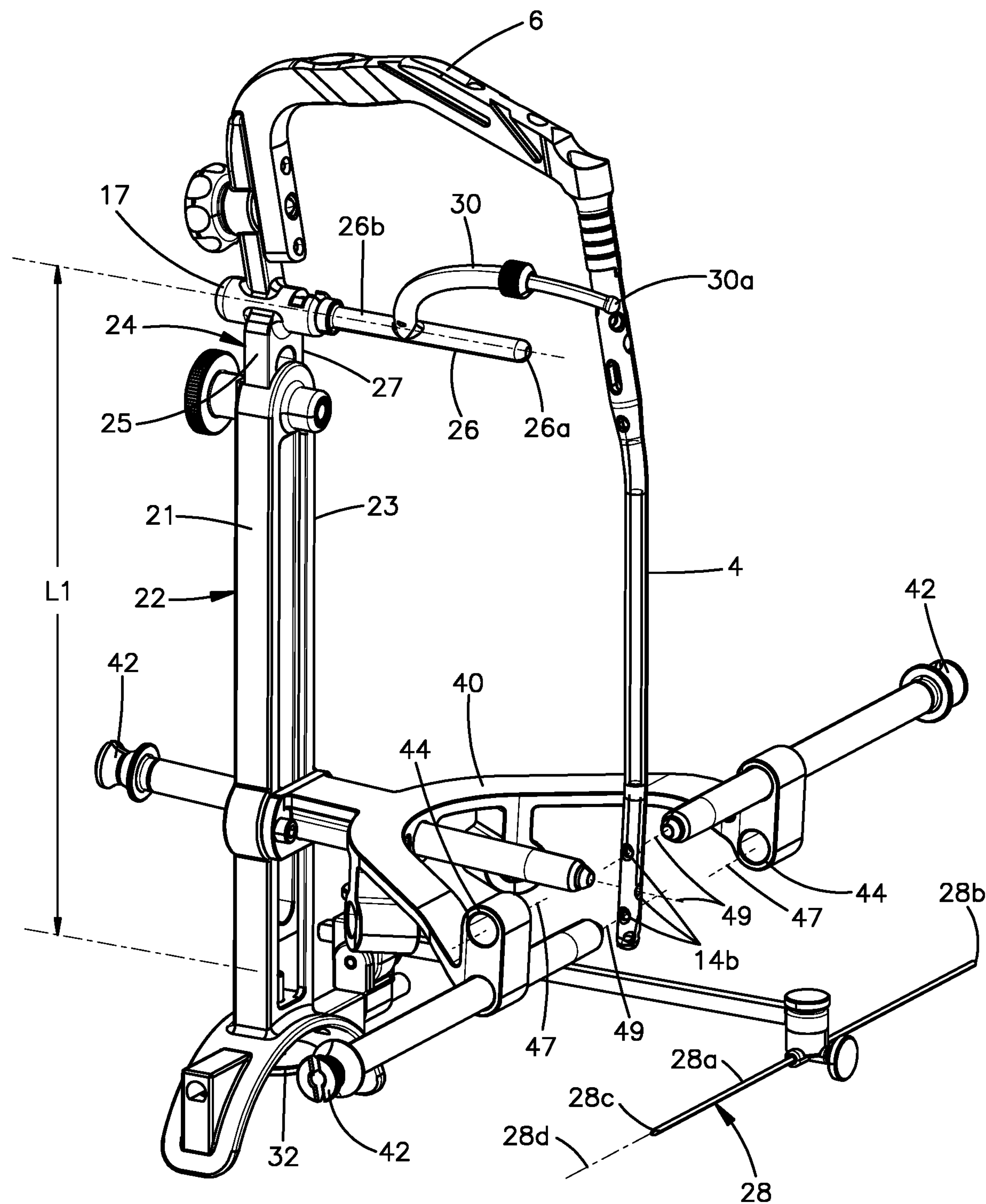
FIG. 2 is a perspective view of the system illustrated in FIG. 1.

Referring now to FIGS. 1 and 2, an exemplary embodiment of an intramedullary implantation system 2 for implanting a bone anchor, such as an intramedullary nail 4, within the medullary canal of a long bone of a patient includes an aiming device 12 that is connectable with the intramedullary nail 4. The aiming device 12 is configured for targeting locking holes of the intramedullary nail from a location external of the patient anatomy, as described in more detail below. The exemplary embodiments illustrated throughout the Figures are configured for intramedullary implantation within the tibia; however, it should be appreciated that the principals of design and operation of the exemplary system 2 can be employed for intramedullary implantation within other bones, including the fibula, femur, humerus, radius, and ulna, for example.

The system 2 includes an insertion instrument, such as an insertion handle 6, that is configured to couple with the intramedullary nail 4, preferably at a proximal end 8 of the intramedullary nail 4 opposite a distal end 10 of the nail 4 along a central nail axis 5. The nail 4 defines a length L0 measured from the proximal end 8 to the distal end 10. The nail 4 can also have at least one body portion, such as a proximal body portion 4*a*, that is angularly offset from at least one other body portion, such as a distal body portion 4*b*, at an offset angle A0. The insertion handle 6 is connectable to the aiming device 12. In particular, the insertion handle 6 includes a mounting structure 16 configured to mount to a complimentary mounting structure 18 of the aiming device 12. The aiming device is configured to guide movement of locking members, such as locking screws, into locking holes defined in the intramedullary nail 4. The locking holes include proximal locking holes 14*a* adjacent the proximal end 8 and remote from the distal end 10 of the nail 4. The proximal locking holes 14*a* are configured to receive locking members for proximal locking of the intramedullary nail 4 to the bone, such as cortical bone at the proximal tibial head. The locking holes also include distal locking holes 14*b* adjacent the distal end 10 and remote from the proximal end 8 of the nail 4. The distal locking holes 14*b* are configured to receive locking members for distal locking of the intramedullary nail 4 to the bone, such as cortical bone at the distal tibial head.

The illustrated aiming device 12 is particularly configured for targeting the distal locking holes 14*b* and guiding movement of locking members into the distal locking holes 14*b*. However, it should be appreciated that the aiming device 12 can also be adapted for targeting one or more of the proximal locking holes 14*a*. Additionally or alternatively, the insertion handle 6 can also be configured to be connected to an additional aiming device for targeting the proximal locking holes 14*a*. For example, the mounting structure 16 of the insertion handle 6, in addition to being connectable to the mounting structure 18 of the aiming device, can also be selectively mountable to a complimentary mounting structure of a separate aiming device for targeting the proximal locking holes 14*a*. In such embodiments, the physician can employ the aiming device 12 described throughout this disclosure to target the distal locking holes 14*b*, and can separately employ the additional aiming device described above for targeting the proximal locking holes 14*a*, as needed.

The aiming device 12 includes a guide frame 20 that is elongated along a longitudinal direction L. The guide frame 20 includes a base frame member 22 and an adjustable frame member 24 that are coupled to each other. The base frame member 22 and the adjustable frame member 24 can also be referred to herein as the "base member" 22 and the "adjustable member" 24. The base member 22 and the adjustable member 24 can each also be individually elongate along the longitudinal direction L. The base member 22 can define first and second opposed sides 21, 23 spaced from each other along a lateral direction A perpendicular to the longitudinal direction L. The adjustable member 24 can also define first and second opposed sides 25, 27 spaced from each other along the lateral direction A. The base member 22 and the adjustable member 24 are coupled to each other in such a manner that the adjustable member 24 is positionally adjustable relative the base member 22 along the longitudinal direction L. For example, the adjustable member 24 is configured to translate relative to the base member 22 along a longitudinal axis 15, which is oriented along the longitudinal direction L, while the base member 22 and the adjustable member 24 are coupled to each other. In this manner, a length L1 of the guide frame 20, such as a length measured between respective portions of the adjustable member 24 and the base member 22, can be longitudinally adjusted to correspond to a respective length of the patient's limb. Thus, the length L1 of the guide frame 20 can also be longitudinally adjusted in accordance with the length L0 of the intramedullary nail 4 selected for implantation. The guide frame 20 includes a first or primary position adjustment mechanism 29 that is configured to iterate between an unlocked configuration, in which the adjustable member 24 is longitudinally adjustable relative to the base member 22, and a locked configuration, in which the base member 22 and the adjustable member 24 are longitudinally fixed to each other, as described in more detail below. It should be appreciated that any of the adjustment and locking mechanisms described herein can also be referred to as an "adjustment mechanism" or a "locking mechanism."

The system 2 can include a kit having a plurality of intramedullary nails 4 having different characteristics, such as different lengths L0, diameters, and/or offset angles A0, by way of non-limiting examples. The lengths L0 of the intramedullary nails 4 in the kit preferably differ from one another by regular length intervals, such as 5.0 mm, 10.0 mm, 15.0 mm, or 20.0 mm, by way of non-limiting examples, allowing a physician to select from the kit the intramedullary nail 4 having the length L0 most suitable for the surgical needs of the patient.

The guide frame 20 and the insertion handle 6 are cooperatively configured to position the intramedullary nail 4 so that the central nail axis 5 is spaced from the longitudinal axis 15 along a transverse direction T that is perpendicular to the longitudinal and lateral directions L, A. The guide frame 20 preferably defines a central reference plane P1 that extends along the longitudinal and transverse directions L, T. Preferably, the longitudinal axis 15 is centrally defined by the guide frame 20 with respect to the transverse direction T, such that the central reference plane P1 extends along the longitudinal axis 15. Moreover, the guide frame 20 is preferably configured to position the intramedullary nail 4 so that the central reference plane P1 also extends along the central nail axis 5. In this manner, components of the aiming device 12 can be repositioned on the guide frame 20 symmetrically about the central reference plane P1 (i.e., symmetrically on opposite sides of the central reference plane P1), thereby accounting for contralateral symmetry between the template limb and the implant limb, as needed.

It should be appreciated that when a limb of the patient is engaged with the aiming device 12, the longitudinal direction L substantially coincides with the cranial-caudal direction of the limb, the lateral direction A substantially coincides with the medial-lateral direction of the limb, and the transverse direction T substantially coincides with the anterior-posterior direction of the limb. Accordingly, any reference plane extending along the longitudinal and transverse directions L, T, such as the central reference plane P1, substantially coincides with a sagittal plane SP of the patient. Additionally, any reference plane extending along the longitudinal and lateral directions L, A substantially coincides with a coronal plane CP of the patient, and any reference plane extending along the lateral and transverse directions A, T substantially coincides with a transverse plane TP of the patient. The transverse plane TP and any plane parallel therewith can also be referred to as a horizontal plane.

The base member 22 can include a receptacle 34 configured to receive a portion of the limb, preferably a base anatomical portion of the limb, such as an extremity thereof (e.g., a foot or hand). In the illustrated embodiment, the receptacle 34 is configured to receive the patient's foot. The receptacle 34 can be defined by a base structure 36 of the base member 22. As shown, the base structure 36 can be configured so as to provide the receptacle 34 with an arch-shaped profile. The base structure 36 can be configured to rest upon a floor or, in instances where the surgical procedure is performed in the "field," the base structure 36 can be configured to rest upon the ground or other supporting surface. The base structure 36 can optionally be configured to provide the guide frame 20 with free-standing capability. In such optional embodiments, the base structure 36 can also be referred to as a "frame stand" or simply a "stand."

The aiming device 12 includes a targeting guide member 40, such as a drill guide 40, that is connectable to the guide frame 20 and is configured to carry one or more guide members, such as guide sleeves 42, in a manner aligning the guide sleeves 42 with the locking holes of the intramedullary nail 4 when the drill guide 40 and the nail 4 are both coupled to the guide frame 20. In particular, the drill guide 40 of the illustrated embodiment is a distal drill guide 40 for targeting the distal locking holes 14*b*, although it should be appreciated that the drill guide 40 can optionally be adapted for use targeting the proximal locking holes 14*a* of the intramedullary nail 4. The drill guide 40 includes a drill guide body 41, which can include a mounting formation 43 configured to mount to a complimentary mounting structure 45 of the base member 22. The drill guide body 41 can define a plurality of guide channels 44 configured for targeting the distal locking holes 14*b* of the nail 4. For example, each guide channel 44 defines a central axis 47 configured to target (i.e., extend through) a respective distal locking hole 14*b*. The guide channels 44 can also be configured to receive the guide sleeves 42 in complimentary fashion. The guide sleeves 42 each define a central axis 49 configured to be coincident with the central axis 47 of the associated guide channel 44. It should be appreciated that the central axes 47, 49 of the guide channels 44 and guide sleeves 42 can each be referred to as a "target axis" or "targeting axis". The plurality of guide channels 44 can include a first subset of the guide channels 44 that are positioned on the first side of the central reference plane P1 and are positioned and oriented symmetrically about the central reference plane P1 from a second subset of the guide channels 44 on that are positioned on the second side of the central reference plane P1. An additional subset of the guide channels 44 can extend along the central reference plane P1.

The guide sleeves 42 are cannulated for guiding movement of one or more instruments therethrough, such as, by way of non-limiting examples: a scalpel or other instrument for making a stab incision in the limb; a drill bit for drilling through the near cortex of the bone in which he nail 4 is inserted, and optionally to and through the associated locking hole 14*b* of the nail 4, and further optionally into and/or through the far cortex of the bone; and a driver carrying the locking member, such as a locking screw, for driving the locking member through the near cortex and through the locking hole 14*b* and preferably into and/or through the far cortex. It should be appreciated that each and every one of the guide channels 44 need not target a respective locking hole 14*b* of the intramedullary nail 4. For example, the drill guide 40 can define more or fewer guide channels 44 than there are distal locking holes 14*b* in the nail 4. It should also be appreciated that one or more and up to all of the guide sleeves 42 can be configured to extend through an outer sleeve, which can also be referred to as a "protection sleeve", which can be received within the respective guide channel 44.

The aiming device 12 includes a plurality of reference members that are each configured to contact a select exterior location on each of corresponding left and right limbs of a patient (i.e., the template limb and the implant limb). Such exterior locations of the limbs can also be referred to as anatomical "reference points", "touch points", or "landmarks". One or more of the reference members is also positionally adjustable relative to the guide frame 20 to account for variations in patient anatomy, including such variations between patients and also variations between the left and right limbs of a single patient. In a first mode of operation of the aiming device 12, in which the guide frame 20 is engaged with the template limb, the reference members are employed to define or otherwise indicate relative positions between the guide frame 20 and the respective landmarks of the template limb, which relative positions can cumulatively define or otherwise indicate an overall relative position between the guide frame 20 and the template limb, including the spatial dimensions and orientation of the limb, including rotation or articulation (e.g., flexion/extension) of the joints thereof (e.g., knee and ankle, with respect to the tibial example)) and the guide frame 20. Subsequently, in a second mode of operation of the aiming device 12, in which the guide frame 20 is engaged with the implant limb, the reference members are employed to substantially replicate the relative position of the template limb on the implant limb in symmetrical fashion about the central reference plane P1, thereby accounting for contralateral symmetry between the template limb and the implant limb. When the intramedullary nail 4 is implanted in the implant limb and mounted to the adjustable member 24 via the insertion handle 6, and also when the drill guide 40 is mounted to the base member 22, the relative position between the guide frame 20 and the implant limb also defines or otherwise indicates relative positions between the target axes 47, 49 of the drill guide 40 and the distal locking holes 14*a* of the nail 9.

In the illustrated embodiment, the aiming device 12 includes a first reference member 26, which can be carried by the adjustable member 24, and a second reference member 28, which can be carried by the base member 22. The aiming device 12 can also include a third reference member 30, which can be carried by the adjustable member 24, and a fourth reference member 32, which can be carried by the base member 22. The first reference member 26 can be a rod, shaft, bar, dowel, or the like, and can extend along a central axis 26*b* oriented along the transverse direction T, as shown. In other embodiments, the central axis 26*b* can at least be oriented along a direction having a directional component along the transverse direction T. The second reference member 28 can also be a rod, shaft, bar, dowel, or the like, and can extend along a central axis 28*d*, which can be oriented along the lateral direction A, or at least along a direction having a directional component along the lateral direction A. The third reference member 30 can be a curved rod, shaft, bar, dowel, or the like, and can be elongate along a direction having directional components along two or all three of the transverse, lateral directions, and longitudinal directions T, A, L. The fourth reference member 32 can be a threaded member, such as a screw or bolt member, that extends through a threaded bore of the base member 22 along the longitudinal direction L.

In the illustrated embodiment, the first reference member 26 is mounted to a targeting formation 17 of the adjustable member 24. The first reference member 26 has a contact portion, such as a contact end or tip 26*a*, that is configured to be placed into contact with a first, proximal landmark of the patient's lower leg, such as the anterior-most point of the proximal tibial head, for example. Other non-limiting examples of the first landmark include the tibial tuberosity, the anterior intercondylar area, or the anterior attachment of the medial meniscus, by way of non-limiting examples. The first reference member 26 can be employed as a primary reference member, such as for setting a baseline relative position between the leg and the guide frame 20. The first reference member 26, or at least the location of its contact portion 26*a*, can be configured to remain positionally fixed relative to the adjustable member 24. Thus, in such embodiments, when the intramedullary nail 4 and insertion handle 6 are mounted to the adjustable member 24, the relative position between the intramedullary nail 4 and the contact portion 26*a* of the first reference member 26 also remains substantially positionally fixed. Accordingly, the first reference member 26 also defines, measures, or otherwise indicates a relative position between the intramedullary nail 4 and the base member 22 (and thus also between the intramedullary nail 9 and the drill guide 40 when the drill guide 40 is coupled to the base member 22). Thus, when the intramedullary nail 4 and the drill guide 40 are coupled to the guide frame 20, the first reference member 26 also defines, measures, or otherwise indicates relative positions between the distal locking holes 14*b* of the nail 4 and the targeting axes 47, 49 of the drill guide 40 and guide sleeves 42, respectively. Accordingly, one or more and up to all of the other reference members can be calibrated with respect to the first reference member 26.

The second reference member 28 has a second contact portion that is configured to be placed into contact with a second, distal landmark of the lower leg. In this manner, the second reference member 28 can be employed to define a relative position between the guide frame 20 and the second landmark of the leg. The second contact portion can be an anterior-facing portion of an outer cylindrical surface 28*a* of the second reference member 28, by way of a non-limiting example. For such a second contact portion (i.e., the anterior-facing portion of the outer cylindrical surface 28*a*), the second landmark targeted thereby can be the posterior apex of the heel, by way of a non-limiting example. Alternatively, either a first end 28*b* or an opposite second end 28*c* of the second reference member 28 can be employed as the second contact portion, such as for contacting the posterior apex of the heel or optionally a medial or lateral portion of the distal third of the tibia or the foot, such as the lateral apex of the lateral malleolus of the ankle, by way of a non-limiting example.

The third reference member 30 has a third contact portion 30*a* configured to be placed into contact with a third landmark of the leg, such as the lateral-most or medial-most portion of the knee, by way of non-limiting examples. In this manner, the third reference member 30 can be employed to define a relative position between the guide frame 20 and the third landmark of the leg. The third contact portion 30*a* can be an outer end of the third reference member 30 spaced from an inner end 30*b* thereof. It should be appreciated that the third reference member 30 is preferably configured to contact a third landmark particularly selected so that the third reference member 30 defines, measures, or otherwise indicates an angle of flexion/extension of the knee. For example, the first landmark can be located on the lower or distal portion of the leg, such as a location associated with the tibia, such as the proximal head thereof, and the third landmark can be located on the upper or proximal portion of the leg, such as a location associated with a portion of the knee or femur spaced proximally (i.e., in the cranial direction) from the tibia, such that the first and third landmarks (and/or the first, second, and third landmarks) collectively indicate a degree of flexion/extension of the lower or distal portion of the limb (i.e., the lower arm or lower leg) relative to the respective proximal portion of the limb (i.e., the upper leg or upper arm) about a joint (i.e., the knee or elbow) located intermediate the first and third landmarks.

The fourth reference member 32 has a fourth contact portion 32*a*, such as at the distal end of the fourth reference member 32 (see, e.g., FIG. 3B) and configured to be placed into contact with a fourth, distal landmark of the lower leg, such as a top surface of the foot received within the receptacle 34, by way of a non-limiting example. The fourth reference member 32 can thus be employed to define a relative position between the guide frame 20 and the fourth landmark of the leg. The fourth reference member 32 can extend from a portion of the base structure 36 into the receptacle 34. The fourth contact portion 32*a* can optionally be located at a distal end of the fourth reference member 32.

It should be appreciated that the guide frame 20 can carry one or more additional reference members for contacting one or more additional landmarks of the limb.

One or more of the reference members 26, 28, 30, 32 are positionally adjustable relative to the guide frame 20 so as to be brought into contact with the respective landmark(s) while the foot is positioned within the receptacle 34. Additionally, one or more of the reference members, such as the second and third reference members 28, 30, for example, can also be configured to be repositioned on the guide frame 20 symmetrically about the central reference plane P1 to account for contralateral symmetry of the template limb and implant limb. In particular, one or both of the second and third reference members 28, 30 can be positioned on a first side of the central reference plane P1 during the first mode of operation (i.e., while engaged with the template leg), and can be repositioned to occupy the mirror image location on a second, opposite side of the central reference plane P1 during the second mode of operation (i.e., while engaged with the implant leg), as described in more detail below.

Figures 3A, 3B:
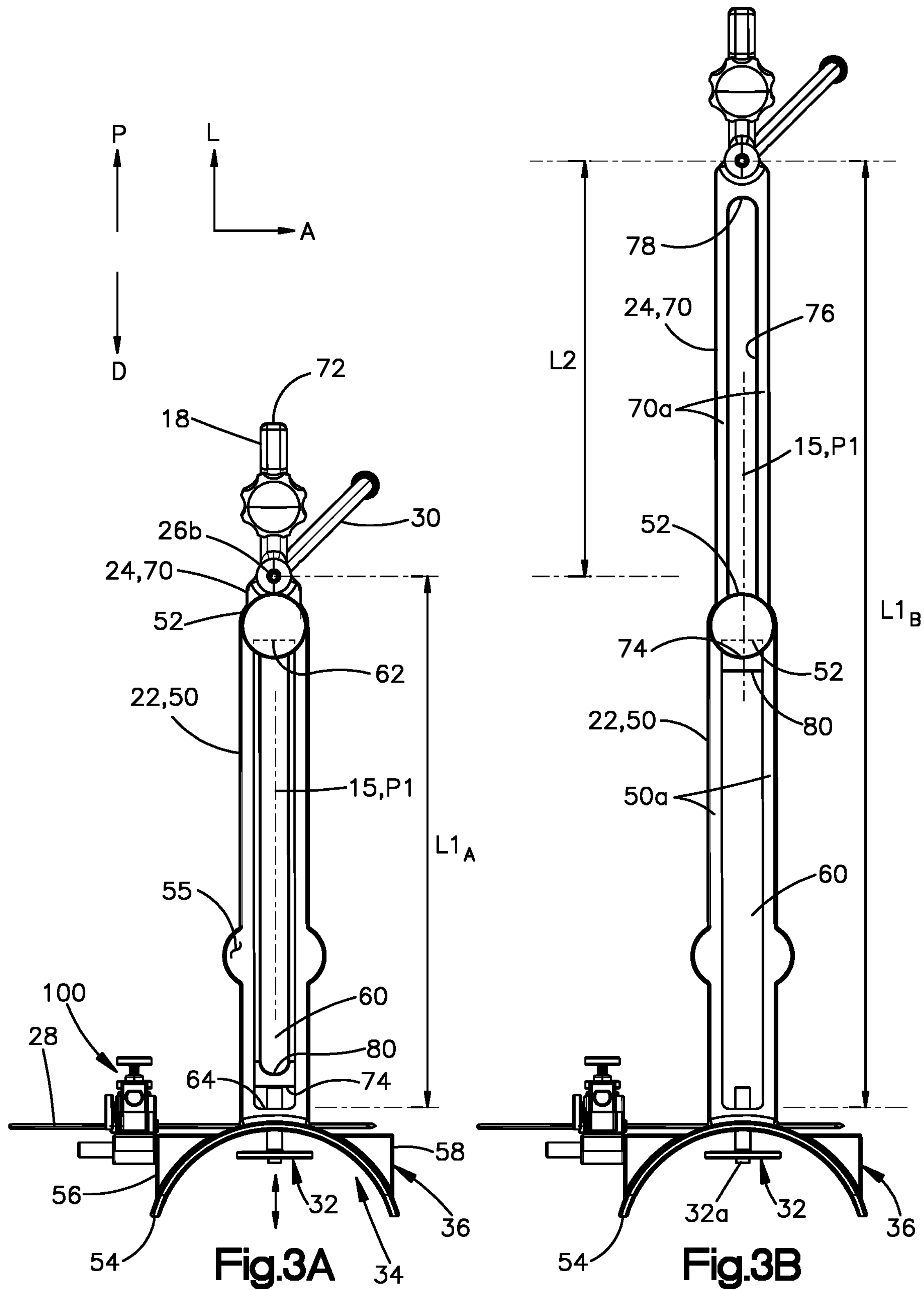
FIG. 3A is a front view of an expandable guide frame of the aiming device shown in FIG. 1, shown at a minimum-length configuration.
FIG. 3B is a front view of the expandable guide frame of FIG. 3A at a maximum-length configuration.

Referring now to FIGS. 3A and 3B, the guide frame 20 is configured so that the adjustable member 24 is configured to translate relative to the base member 22 longitudinally (i.e., along the longitudinal direction L), as described above. The base member 22 has a body 50 that defines a first or proximal end 52 and a second or distal end 54 spaced from the proximal end 52 in a distal direction D. The proximal end 52 is spaced from the distal end 54 in a proximal direction P opposite the distal direction D. It should be appreciated that the proximal and distal directions P, D are each monodirectional components of the longitudinal direction L, which is bi-directional. The base member body 50 has a front or anterior face 55 that faces in the anterior direction. The base structure 36, which defines the receptacle 34, is located at the distal end 54 of the base member body 50. The base structure 36 has a first lateral side 56 and an opposed second lateral side 58 laterally spaced from each (i.e., spaced from each other along the lateral direction A). The second reference member 28 is carried by a positioning assembly 110 mounted to the base structure 36. Preferably, the positioning assembly 110 can be selectively mounted to either of the first and second lateral sides 58 of the base structure 36, as described in more detail below. The base member body 50 can define a channel 60 that is elongate along the longitudinal direction L and configured to receive a portion of the adjustable member 24. Preferably, the channel 60 is centrally defined by the base member body 50 with respect to the lateral direction A (i.e., the central reference plane P1, and thus also the longitudinal axis 15, extends longitudinally through the center of the channel 60). The base member body 50 can thus include a pair of arms 50*a* extending longitudinally on the lateral sides of the channel 60. The channel 60 has a first or proximal end 62 and a second or distal end 64 each defined by the base member body 50 and longitudinally spaced from each other.

The adjustable member 24 has a body 70 that defines a first or proximal end 72 and a second or distal end 74 longitudinally spaced from each other. The mounting structure 18 for mounting with the insertion handle 6 can extend to the proximal end 72 of the adjustable member body 70. The adjustable member body can define a channel 76 that is elongate along the longitudinal direction L and centrally located with respect to the lateral direction A. In this manner, features of the aiming device and/or anatomical features of the patient can be viewed by a physician from an anterior side of the guide frame 20. The adjustable member body 70 can also include a pair of arms 70*a* extending longitudinally on the lateral sides of the channel 76. The channel 76 has a first or proximal end 78 and a second or distal end 80 longitudinally spaced from each other and each defined by the adjustable member body 70. The proximal end 62 of the channel 60 of the base member body 50 can be a first or proximal translation stop member configured to abut the proximal end 72 of the adjustable member body 70 in a manner limiting longitudinal translation between the adjustable member body 70 and the base member body 50. The adjustable member body 70 is preferably configured to translate longitudinally relative to the base member body 50 between a minimum length $L1_A$, as shown in FIG. 3A, to a maximum length $L1_B$, as shown in FIG. 3B. Accordingly, a range of longitudinal translation L2 of the adjustable member 24 relative to the base member 22 is defined by the difference between the maximum and minimum lengths $L1_B$, $L1_A$ (i.e., $L2=L1_B-L1_A$). The minimum length $L1_A$ can be in a range from about 75 mm to about 300 mm, and the maximum length $L1_B$ can be in a range from about 350 mm to about 550 mm, by way of non-limiting examples. The range of longitudinal translation can be from about 15 mm to about 250 mm, and more particularly from about 100 mm to about 200 mm, and preferably at least about 150 mm. It should be appreciated that lengths L1, $L1_A$, $L1_B$ and range L2 can be measured between respective portions of the adjustable member 24 and the base member 22 and/or portions of components carried thereby. For example, the lengths L1, $L1_A$, $L1_B$ and range L2 can be measured between the central axis 26*b* of the first reference member 26 and the distal end 64 of the channel 60 of the base member 22, by way of a non-limiting example.

Figure 4:
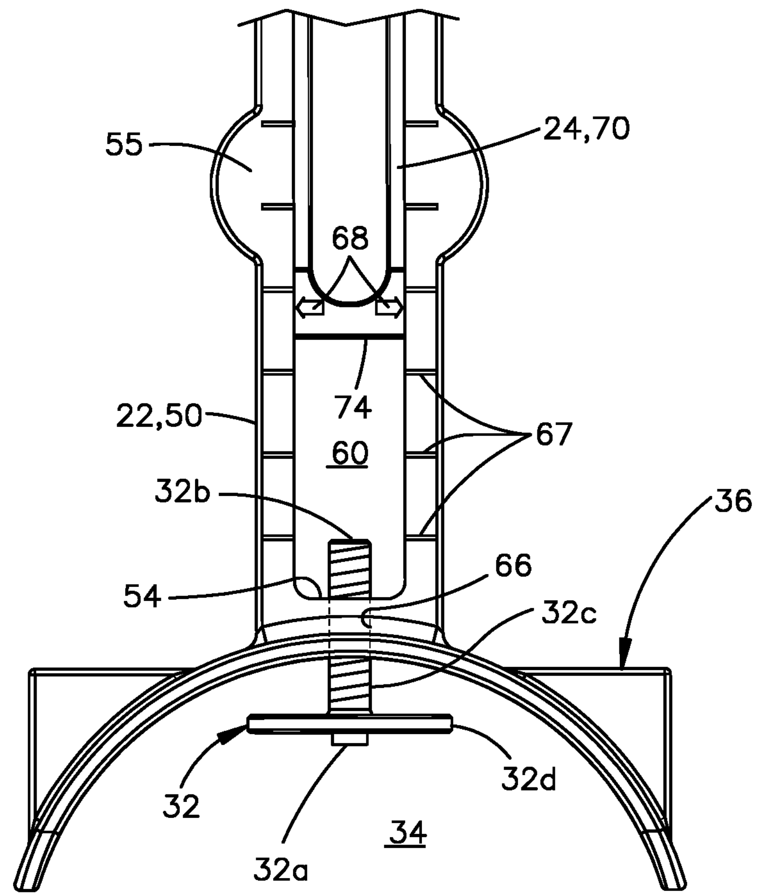
FIG. 4 is a front view of a face of a portion of the expandable guide frame shown in FIG. 1.

Referring now to FIG. 4, the fourth reference member 32 can have a proximal end 32*b* configured to reside in the channel 60 while the fourth contact portion 32*a* at the distal end of the fourth reference member 32 resides in the receptacle 34. The fourth reference member 32 can also have a threaded shaft 32*c* that extends through a complimentary threaded longitudinal bore 66 defined between the distal end 64 of the channel 60 and the receptacle 34. The threaded shaft 32*c* preferably has a length sufficient to allow the proximal end 32*b* to reside in the channel 60 while the contact portion 32*a* resides in the receptacle 34. The fourth reference member 32 can also include a knob 32*d* at or adjacent the contact portion 32*a*. The knob 32*d* can be rotated to adjust the longitudinal position of the fourth reference member 32, including the contact portion 32*a* and proximal end 32*b*, relative to the distal end 64 of the channel 60 and also relative to the receptacle 34. The fourth reference member 32 can be adjusted longitudinally relative to the base member body 50 as needed, such as to effectively position the distal end 10 of the intramedullary nail 4 at a desired longitudinal position within the medullary canal. It should be appreciated that when the proximal end 32*b* of the fourth reference member 32 extends within the channel 60, the proximal end 32*b* can define an abutment surface of a second or distal translation stop member configured to abut the distal end 74 of the adjustable member body 70 in a manner limiting the range of longitudinal translation L2. Thus, the fourth reference member 32 can adjust the minimum length $L1_A$ of the guide frame 20 and the range of longitudinal translation L2. The front face 55 of the base member body 50 can include visual indicia, such as graduated hash marks 67 at regular length intervals, such as 15.0 mm, along the front face 55, by way of a non-limiting example. The adjustable member body 70 can also include corresponding visual indicia, such as baseline arrows 68, by way of a non-limiting example, to reference the hash marks 67 in a manner indicated the precise relative longitudinal position between the base member body 50 and the adjustable member body 70. It should be appreciated that the regular length intervals of the visual indicia preferably coincide with the regular length intervals of the intramedullary nails 4 in any kit for use with the system 2.

Figure 5:
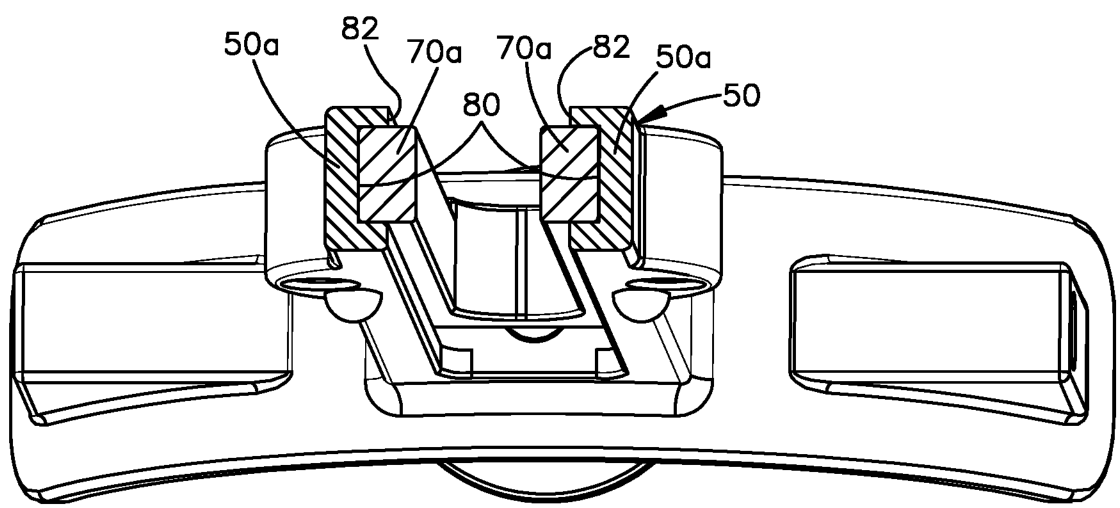
FIG. 5 is a partial sectional perspective view of the guide frame shown in FIG. 1, illustrating complimentary guide features defined by a base frame member and an adjustable frame member of the guide frame, according to an embodiment of the present disclosure.

Referring now to FIG. 5, the base member body 50 and adjustable member body 70 preferably have complimentary guide features to guide translation of the adjustable member body 70 relative to the base member body 50 along the longitudinal direction L. The complimentary guide features are also configured to maintain the orientation between the base member body 50 and the adjustable member body 70 during and after translation, such as by preventing other modes of relative movement between the bodies 70, 50, which could deleteriously affect the alignment of the target axes 47, 49 relative to the distal locking holes 14*b* of the intramedullary nail 4. As shown, the guide features can include guide slots 82 defined in inner wall surfaces 50*b* of the arms 50*a* of the base member body 50. The guide slots 82 have complimentary, conformal geometries with the arms 70*a* of the adjustable member body 70 to guide translation of the adjustable member body 70 relative to the base member body 50 along the longitudinal direction L. It should be appreciated that other conformal geometries between the base and adjustable member bodies 50, 70 are within the scope of the present disclosure.

Figure 6:
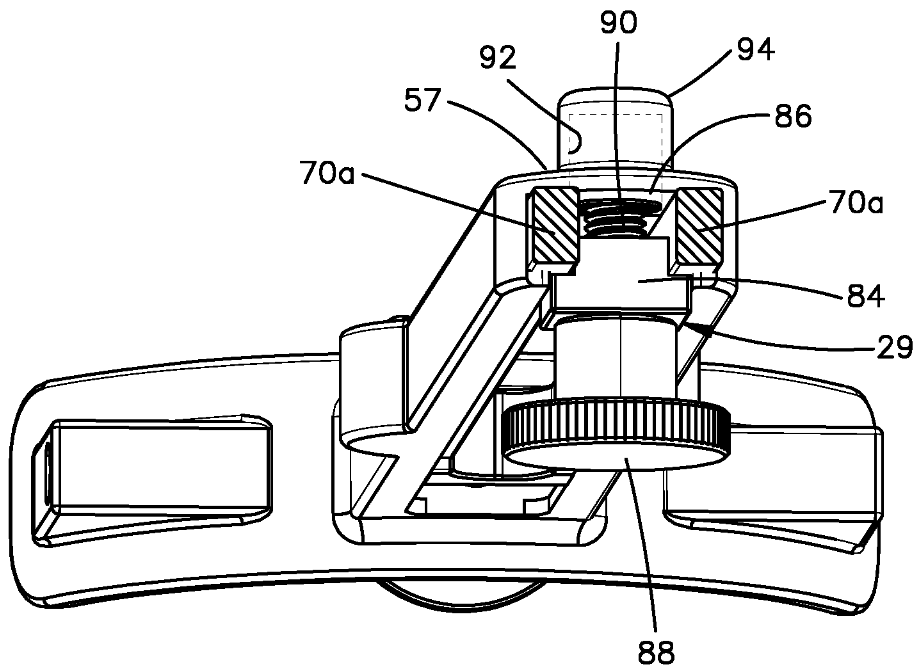
FIG. 6 is a partial sectional perspective view of the guide fame shown in FIG. 5, illustrating a positional adjustment mechanism of the guide frame for adjusting the length of the guide frame, according to an embodiment of the present disclosure.

Referring now to FIG. 6, the primary position adjustment mechanism 29 can be a clamp having a clamp member 84 configured to move between the unlocked configuration, in which the adjustable member body 70 is longitudinally adjustable relative to the base member body 50, and a locked configuration, in which the adjustable member body 70 is fixed to the base member body 50. The clamp member 84 can be configured to press the arms 70*a* of the adjustable member body 70 in the posterior direction against a locking surface 86 facing the anterior direction with sufficient force to inhibit longitudinal translation when in the locked configuration. The position adjustment mechanism 29 can include a control member, such as a knob 88, that is coupled to the clamp member 84 and configured to rotate so as to iterate the clamp member 84 between the unlocked and locked configurations. The knob 88 can be coupled to a threaded shaft 90 that extends transversely (i.e., along the transverse direction T) from the knob 88, through an unthreaded bore defined by the clamp member 84 and into a threaded bore 92 defined by a receptacle member 94 extending from a posterior face 57 of the base member body 50. Complimentary threaded engagement between the threaded shaft 90 and the threaded bore 92 translates the threaded shaft, and thus also the knob 88 and thus also the clamp member 84, between the locked and unlocked configurations to adjust length of extension of the adjustable member body 70 relative to the base member body 50.

Figure 7A:
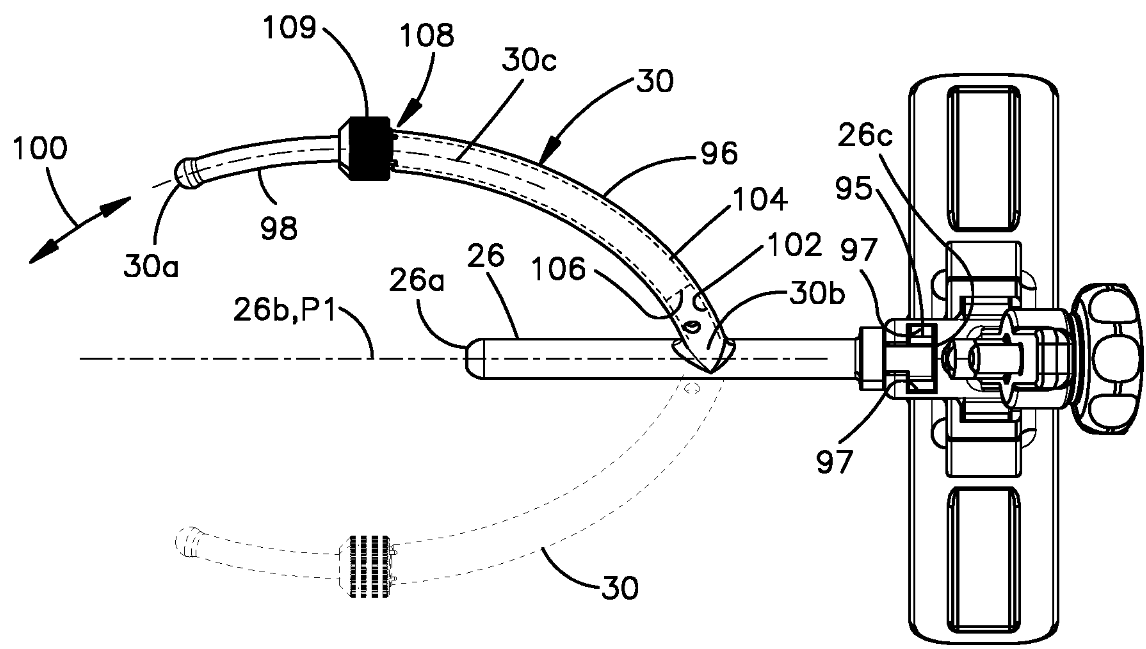
FIG. 7A is a top view of the guide frame shown in FIG. 1, illustrating first and third reference members of the guide frame each for contacting a respective location of a patient's limb.
Figure 7B:
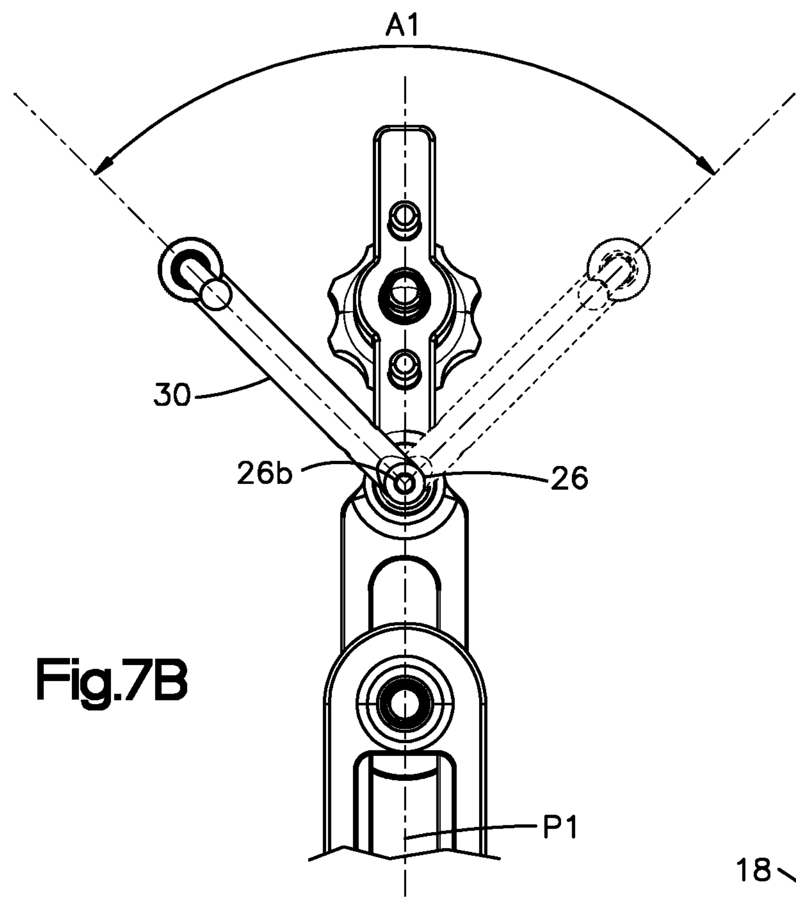
FIG. 7B is a front view of the first and third reference members illustrated in FIG. 7A.

Referring now to FIGS. 7A and 7B, the third reference member 30 can extend outwardly and arcuately from the first reference member 26, such as from a location thereof between the contact end 26*a* and a second end 26*c* opposite the contact end 26*a* along the transverse direction T. The third reference member 30 extends along a central axis 30*c*. The first reference member 26 is preferably configured to rotate about its central axis 26*b* between a first maximum rotational position (as indicated by the solid-line version of the third reference member 30) and a second rotational position (as indicated by the dashed-line version of the third reference member 30), thereby repositioning the third reference member 30 symmetrically about the central reference plane P1 for targeting the third anatomical landmarks on the template and implant limbs. The third reference member 30 can rotate about central axis 26*b* between the first and second maximum rotational positions within a range of angular rotation A1 that can be from about 0 degrees to plus or minus about 90 degrees (i.e., about a 180 degree span), and more particularly from about 0 degrees to plus or minus about 45 degrees (i.e., about a 90 degree span), and preferably about 0 degrees to about 30 degrees (i.e., about a 60 degree span). Accordingly, central axis 26*b* can also be referred to as a pivot axis of the third reference member 30.

As shown in FIG. 7A, the first reference member 26 and the targeting formation 17 can include complimentary features for limiting the first and second maximum rotational positions. For example, the first reference member 26 can define a tab or protrusion 95 located at or adjacent the second end 26*c* and extending outwardly along a radial direction perpendicular to the central axis 26*b*. The protrusion 95 can be configured to abut respective, opposed stop surfaces 97 of the targeting formation 17 at the first and second maximum rotational positions.

The third reference member 30 preferably includes a first or anterior body 96, which can extend from the first reference member 26, and an extendable second or posterior body 98 that is configured to extend outwardly from the first body 96 along a direction 100 along the central axis 30*c*. The direction 100 can thus be referred to as an axial direction. The extendable body 98 is preferably configured to move along the axial direction 100 relative to the first body 96 so as to adjust the position the third reference member 30*a* along the central axis 30*c* as needed to target the third landmark. For example, the first body 96 can be a sleeve defining a central bore 102, and the extendable body 98 can have an outer surface 104 complimentary with the central bore 102 so that the central bore 102 guides movement of the extendable body 98 along the axial direction 100. The extendable body 98 can extend from a first end 106 thereof to the contact end 30*a*. The third reference member 30 can also include a position adjustment mechanism 108 that is configured iterate between a locked position, in which the extendable body 98 is fixed relative to the first body 96, and an unlocked position, in which the extendable body 98 is movable relative to the first body 96 along the axial direction 100. In the illustrated embodiment, the position adjustment mechanism 108 includes a locking collar 108, which is configured to iterate between the locked and unlocked positions by rotating in opposite rotational directions about the central axis 30*c* of the third reference member 30 so as to lockingly engage and disengage the outer surface 104 of the extendable body 98. It should be appreciated, however, that other types of position adjustment mechanisms can be employed with the third reference member 30.

It should be appreciated that, at the maximum angular position of the third reference member 30 about central axis 26*b*, and at maximum extension of the extendable body 98 relative to the first body 96 along the axial direction 100, the third contact portion 30*a* can be coincident with the central reference plane P1, or optionally even extend across the central reference plane P1. In this manner, the third reference member 30 can provide the physician with flexibility in selecting the third landmark.

Figure 7C:
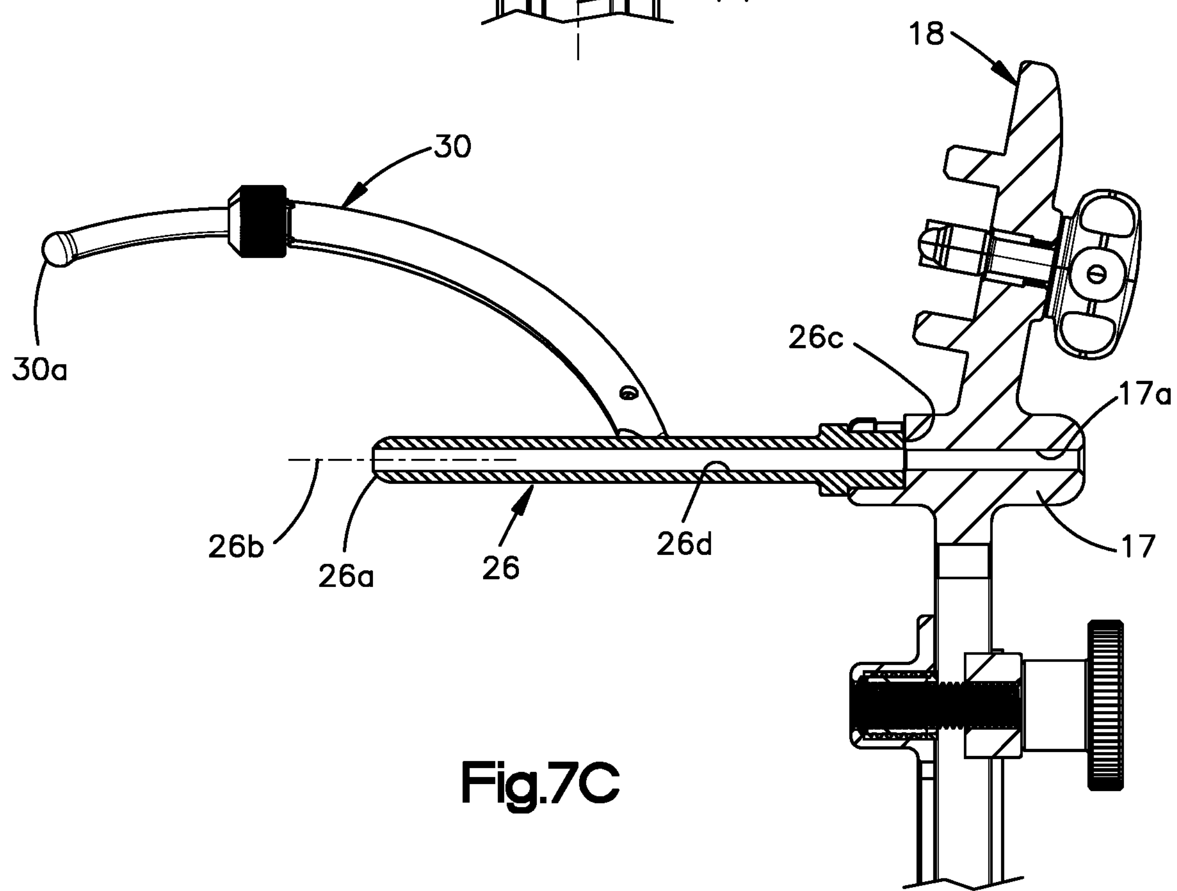
FIG. 7C is a sectional side view of the first reference member illustrated in FIG. 7A.

Referring now to FIG. 7C, the first reference member 26 can define a cannulation 26*d* extending from the second end 26*c* to the contact end 26*a* along the central axis 26*b*. The cannulation 26*d* can be aligned with, and in communication with, a cannulation 17*a* defined by the targeting formation 17. It should be appreciated that the cannulations 17*a*, 26*d* can optionally be employed for targeting one of the proximal locking holes 14*a* of the intramedullary nail 4.

Figure 8A:
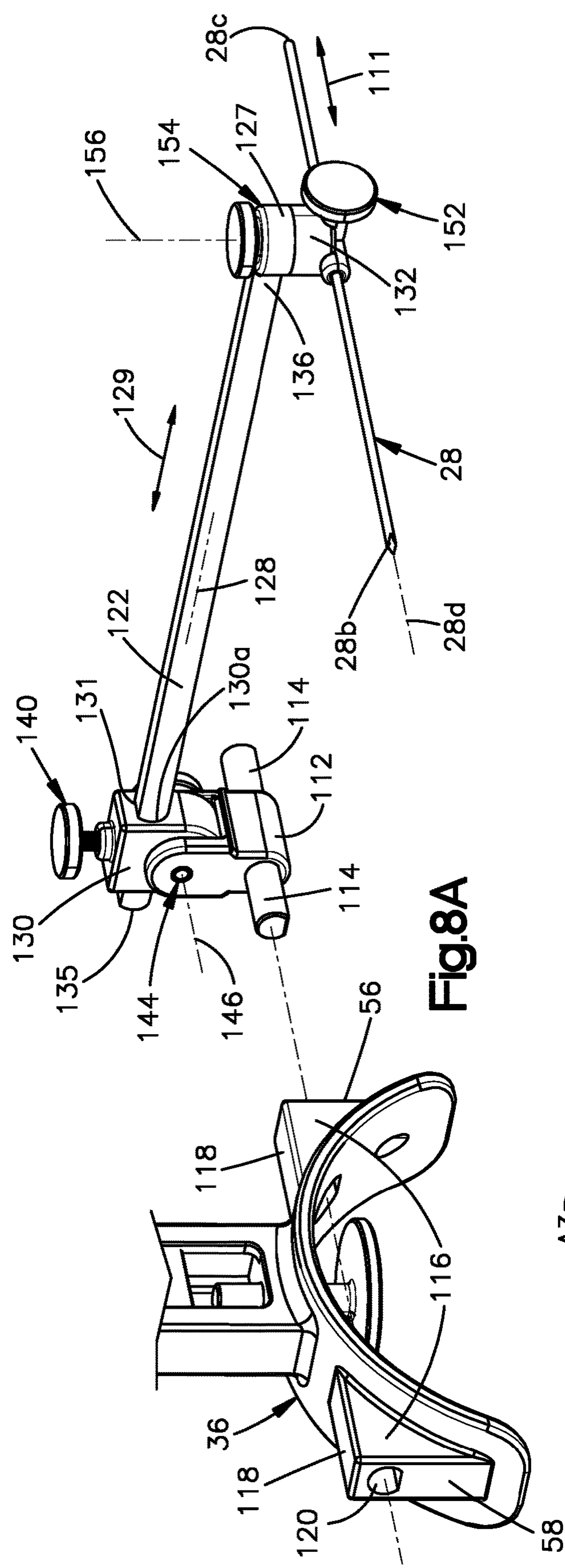
FIG. 8A is a perspective view of a positioning assembly attachable to the guide frame, showing the positioning assembly carrying a second reference member for contacting another respective location of the patient's limb, further illustrating a mounting formation of the positioning for engagement with receiving formations of the guide frame.
Figure 8B:
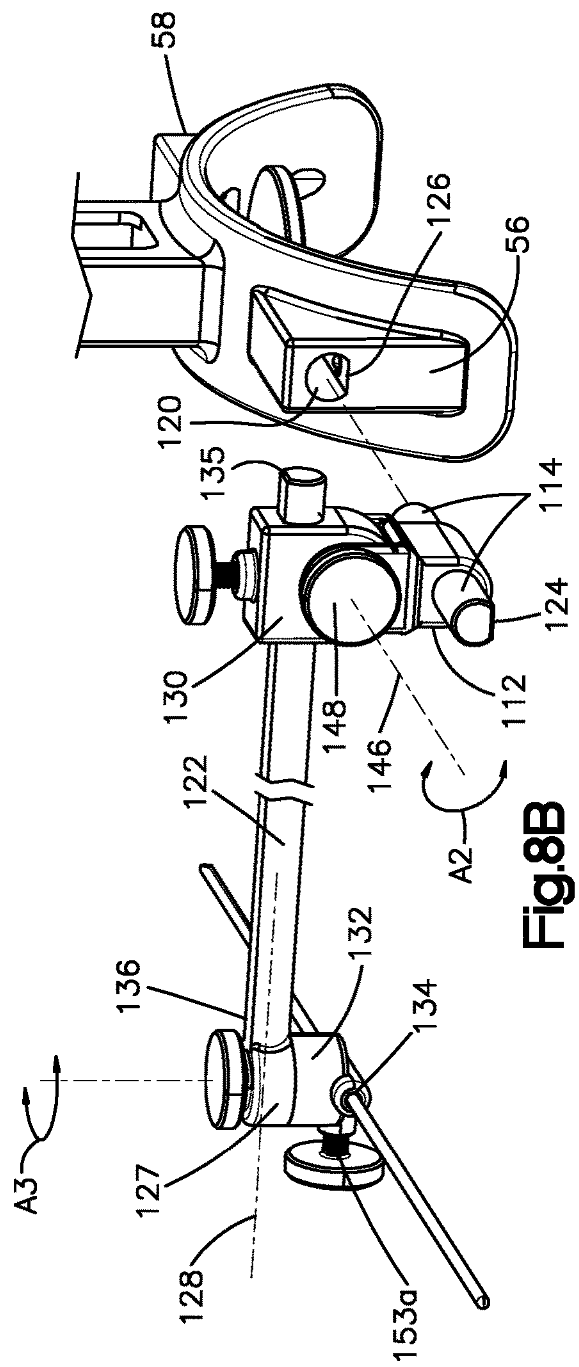
FIG. 8B is another perspective view of the positioning assembly illustrated in FIG. 8A.
Figure 8C:
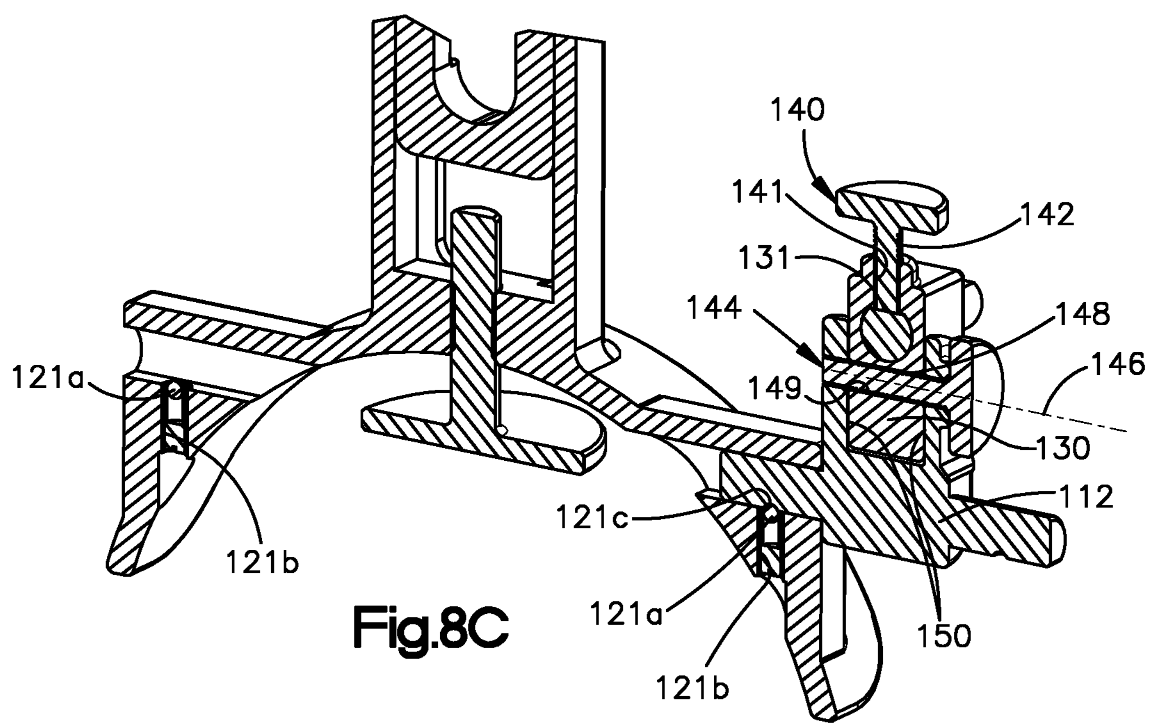
FIG. 8C is a sectional rear view of the positioning assembly and the guide frame illustrated in FIG. 8A.

Referring now to FIGS. 8A and 8B, the positioning assembly 110 is preferably configured to carry the second reference member 28 such that the ends 28*b*, 28*c* thereof are spaced from each other along a direction 111 that is oriented along the lateral direction A or at least has a directional component along the lateral direction A. The positioning assembly 110 is also configured for adjusting the position of the second reference member 28 relative to the base member 22. The positioning assembly 110 can include a mounting formation 112 configured to mount to either lateral side 56, 58 of the base structure 36. The mounting formation 112 can include a pair of mounting posts 114 extending laterally away from each other. The base structure 36 can include a receiving formation 116, such as a pair of shoulders 118 that define the lateral sides 56, 58 of the base structure 36. The shoulders 118 can respectively define a pair of receptacles 120 laterally aligned with each other and having geometries complimentary with those of the mounting posts 114. Those geometries can include respective flat surfaces 124, 126 or "flats" configured to prevent rotation between the mounting posts 114 and the receptacles 120. As best shown in FIG. 8C, the body 50 of the base structure 36 and the mounting posts 114 can employ ball-and-detent mechanisms for releasably anchoring the mounting posts 114 within the receptacles 120. For example, each of the shoulders 118 of the base structure 36 can include a spring-loaded ball 121*a* that is located within a bore 121*b* defined within the shoulder 118 and is configured to extend within complimentary recesses 121*b* defined in the flat surfaces 124 of the mounting posts 114 of the 112 positioning assembly 110. It should be appreciated that the mounting formation 112 of the positioning assembly 110 can mount to either of the receiving formations 118 in the first mode of operation, and can subsequently decouple therefrom and mount to the other receiving formation 118 for use in the second mode of operation.

The positioning assembly 110 includes an arm 122 that is elongate between anterior and posterior ends 135, 136 thereof along an arm axis 128 oriented along an arm direction 129 having a least a directional component along the transverse direction T. The arm 122 is coupled to a first or anterior carrier 130 that is coupled to the mounting formation 112. The anterior carrier 130 can be disposed between a pair of bracket arms 150 of the mounting formation 112 that extend upwardly or proximally therefrom along the longitudinal direction L and are spaced from each other along the lateral direction A. The arm 122 of the positioning assembly 110 is preferably configured to translate relative to the base structure 36 along the arm direction 129. For example, the anterior carrier 130 can define a guide channel 130*a* having a geometry complimentary with a geometry of the arm 122 for guiding translation of the arm 122 therethrough. Thus, the arm 122 can also be translatable relative to the anterior carrier 130 and the mounting formation 112 along the arm direction 129. The arm 122 and the guide channel 130*a* can also have respective flats 131 configured to prevent rotation of the arm 122 relative to the anterior carrier 130 about the arm axis 128. The positioning assembly 110 also includes a second or posterior carrier 132, which can be connected to the posterior end 136 of the arm 122. The posterior carrier 132 is configured to carry the second reference member 28 along direction 111, as described above. For example, the posterior carrier 132 can define a receptacle 134, such as a slot or channel, that is also elongate along the direction 111 and is configured to receive the second reference member 28. The receptacle 134 preferably has a geometry that is complimentary with the outer surface of the second reference member 28. The posterior carrier 132 can be coupled to the posterior end 136 of the arm, as shown in the illustrated embodiment. It should be appreciated, however, that in other embodiments, the posterior carrier 132 can be monolithic with the arm 122.

Referring now to FIGS. 8A through 8D, the positioning assembly 110 includes at least one and preferably a plurality of position adjustment mechanisms allowing precise adjustments to a relative position between the second reference member 28 and the guide frame 20 with respect to at least one and up to three or more directions for targeting the second anatomical landmarks of the template and implant limbs.

As shown in FIGS. 8A through 8C, the positioning assembly 110 can include a first position adjustment mechanism 140, which can be configured for adjusting a relative position between the arm 122 (and thus also the posterior carrier 132) and the mounting formation 112 (and thus also the guide frame 20) along the arm direction 129, particularly for adjusting translation of the arm 122 relative to the anterior carrier 130 along the arm direction 129. The first position adjustment mechanism 140 can include a threaded bore 141 and a set screw 142 threadedly engaged within a threaded bore 141 and configured to engage and disengage the flat 131 of the arm 122 as needed to respectively inhibit and allow translation of the arm 122 along the arm direction 129 relative to the mounting formation 112, as best shown in FIG. 8C.

A second position adjustment mechanism 144 of the positioning assembly 110 can be a pivot joint for pivoting the arm 122 about a lateral pivot axis 146, thereby adjusting a relative position of the arm 122 with respect to the mounting formation 112 along the longitudinal direction L. Thus, the pivot joint 144 can adjust an angular position of the arm axis 128 about pivot axis 146 within a range of angular rotation A2 that can be 360 degrees or larger, or more particularly up to about 180 degrees, or more particularly up to 60 degrees. The pivot joint 144 can include a screw 148 threadedly engaged with a threaded bore 149 extending through the anterior carrier 130 along the lateral pivot axis 146. Rotation of the screw 148 can frictionally lock and unlock rotation of the anterior carrier 130 against one or both of the bracket arms 150 of the mounting formation 112 positioned astride the anterior carrier 130.

Figure 8D:
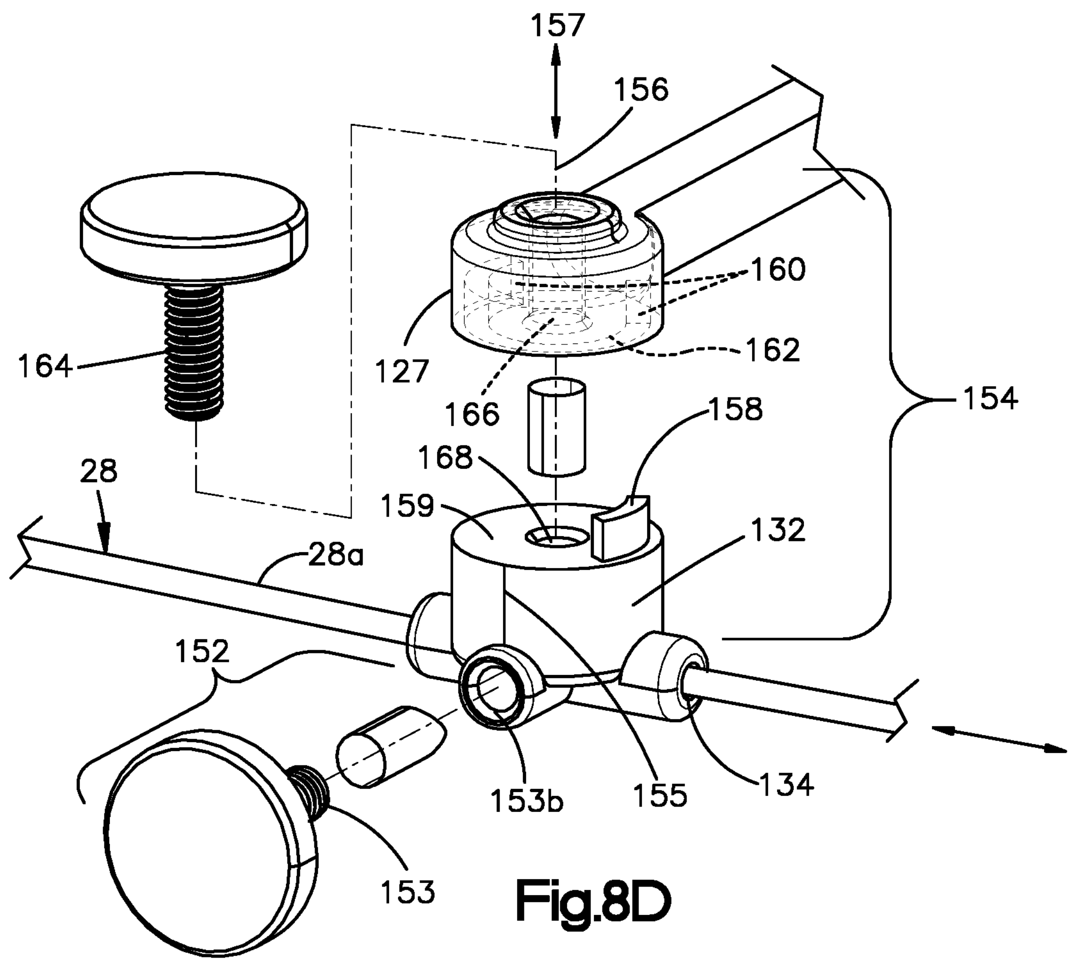
FIG. 8D is an exploded perspective view of an adjustable carrier of the positioning assembly illustrated in FIG. 8A.

As shown in FIGS. 8A, 8B and 8D, the positioning assembly 110 can include a third position adjustment mechanism 152, which can be configured for adjusting a relative position between the second reference member 28 and the posterior carrier 132 (and thus also the mounting formation 112) along direction 111, for example, via translation of the second reference member 28 relative to the posterior carrier 132 along direction 111. As shown, the third position adjustment mechanism 152 can include a set screw 153*a* that is configured to extend through a bore 153*b* in the posterior carrier 132 that is in communication with the receptacle 134 so that the set screw 153 can engage and disengage the outer surface 28*a* of the second reference member 28 as needed to respectively inhibit and allow its translation along direction 111.

The positioning assembly 110 can include a fourth position adjustment mechanism 154 for adjusting a relative position between the second reference member 28 and the mounting formation 112. The fourth position adjustment mechanism 154 can be a pivot mechanism for pivoting the second reference member 28 about a pivot axis 156 oriented along a direction 157 perpendicular to directions 111 and 129. With particular reference to FIG. 8D, the pivot mechanism 154 can include a tab or protrusion 158 that extends upwardly from a platform surface 159 of the posterior carrier 132 along direction 157. The tab 158 can also extend partially circumferentially about pivot axis 156. The tab 158 is configured to iterate between a pair of end surfaces 160 defined within a circumferential slot 162 defined in a posterior end body portion 127 of the arm 122. The respective circumferential distances of the tab 158 and slot 162 (i.e., the angle about which the tab 158 and slot 162 respectively subtend about pivot axis 156) can determine a range of angular rotation A3 of the posterior carrier 132 about axis 156. Preferably, the range of rotation A3 is 180 degrees about the axis 156. In this manner, when the positioning assembly is mounted to the opposite receiving formation 116 of the base structure 36, such as between the first and second modes of operation described above, the posterior carrier 132 can be rotated or toggled 180 degrees about pivot axis 156, thereby repositioning the contact portions 28*a-c* of the second reference member 28 symmetrically about the central reference plane P1, so as to account for contralateral symmetry of the template and implant limbs. It should be appreciated, however, that the range of rotation A3 can be as great as 360 or greater and as small as about 0 degrees, such as from 1 degree to 360 degrees or any intermediate range, for example. The pivot mechanism 154 can include a threaded screw 164 that extends through consecutive bores 166, 168 defined in the posterior end body portion 127 and the posterior carrier 132, respectively. The threaded screw 164 can be rotated as needed to frictionally lock and unlock rotation of the posterior carrier 132 relative to the posterior end body portion 127 with respect to pivot axis 156.

The first, second, third, and fourth position adjustment mechanisms 140, 144, 152, 154 described above allow the physician to make precise and fine adjustments to the position of the second reference member 28 relative to the base member 22 in each of the longitudinal, lateral, and transverse directions L, A, T for targeting the second anatomical landmarks. It should be appreciated, however, that the positioning assembly 110 can optionally include less than each of the first, second, third, and fourth position adjustment mechanisms 140, 144, 152, 154. Stated differently, the positioning assembly 110 need not include each of the first, second, third, and fourth position adjustment mechanisms 140, 144, 152, 154 described above. By way of a non-limiting example, in lieu of the fourth adjustment mechanism 154, the second reference member 28 can include visual indicia, such as graduated hash marks at regular length intervals, along the outer surface 28*a* thereof to indicate a length at which either or both of the respective ends 28*b*, c extends from a centerline 155 of the posterior carrier 132 along direction 111. In such embodiments, instead of pivoting the posterior carrier 132 about pivot axis 156 between the first and second modes of operation, the physician can measure the distance by which the respective end 28*b, c* extends from the centerline 155 along direction 111 when the end 28*b*, c contacts the second landmark of the template limb, and subsequently adjust the translational position of the second reference member 28 for the second mode of operation, using the visual indicia, such that the other end 28*c, b* is spaced from the centerline 155 by the same distance along direction 111. In other embodiments, however, the second reference member 28 can include the visual indicia described above for use in addition to the fourth position adjustment mechanism 154, which can allow the physician the optional of selecting between using the visual indicia or the fourth position adjustment mechanism 154 (or both) to reposition the second reference member 28 as needed between the first and second modes of operation. It should also be appreciated that various combination of the first, second, third, and fourth position adjustment mechanisms 140, 144, 152, 154 can be employed as needed to target the desired second anatomical landmark.

It should be appreciated that the particular reference members 26, 28, 30, 32 described above, and the respective position adjustment mechanisms associated therewith, are provided as non-limiting examples for determining relative positions between those anatomical landmarks and the aiming device for contralateral replication on the implant limb. It should also be appreciated that one or more of the reference members 26, 28, 30, 32 can be adapted to substitute for one or more of the other reference members 26, 28, 30, 32. By way of a non-limiting example, in other embodiments of the present disclosure, the first and third reference members 26, 30 can be replaced by a substantial duplicate of the second reference member 28 and its positioning assembly. Other substitutions are also within the scope of the present disclosure. Furthermore, fewer than or more than the four reference members 26, 28, 30, 32 described above can be employed on the guide frame 20.

Example methods of using the system 2 now be described with reference to FIGS. 9A through 9F. It should be appreciated that although the example methods described below refer to implantation of an intramedullary nail 4 within a tibia, the principals of using the exemplary system 2 described below can be employed for intramedullary implantation within the other long bones, including those described above (e.g., fibula, femur, humerus, radius, and ulna).

Figure 9A:
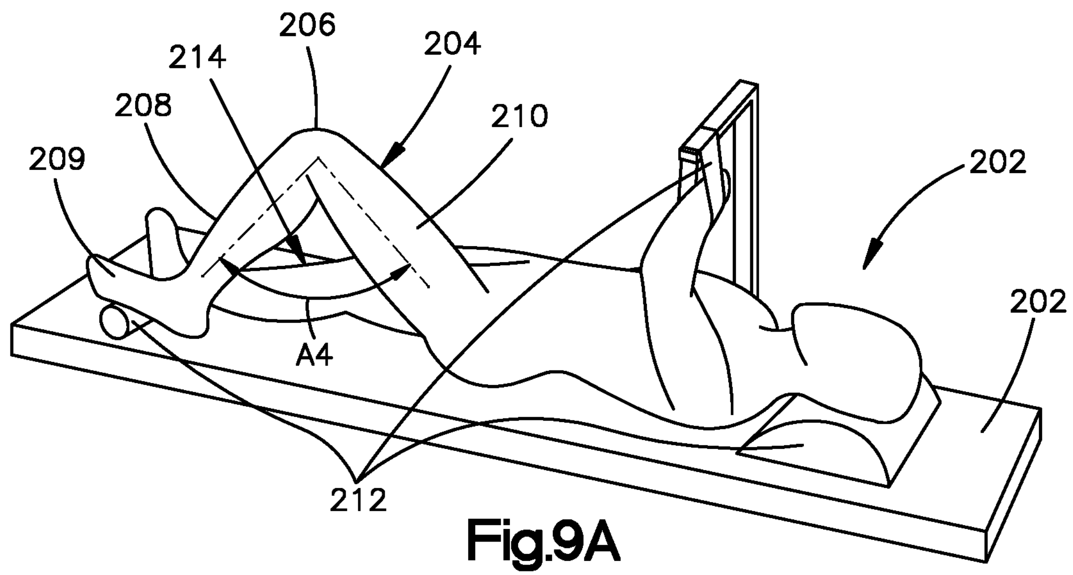
FIG. 9A is a perspective view of a patient positioned on an operating surface in preparation for a procedure using the aiming device illustrated in FIG. 1.

Referring now to FIG. 9A, a patient 200 can be positioned on an operating surface 202, such as an operating table. With the patient 200 on the operating surface 202, the template limb of the patient, indicated by reference numeral 204, can be manipulated, such as manually, into a position suitable for implantation of an intramedullary nail 4 into the medullary canal of the tibia 215. For example, a physician can bend the template leg 204 about the knee 206 such that a lower or distal portion 208 of the template leg 204 (i.e., the "lower leg" portion 208 thereof, that is, the portion below the knee 206) is at a desired angle of flexion/extension A4 relative to an upper or proximal portion 210 of the template leg 204 (i.e., the "upper leg" portion 210 thereof, that is, the portion above the knee 206). One or more external positioning elements 212, such stirrups, traction straps, pads, rollers and the like, can be employed as needed to manipulate and maintain the template leg 204 into the desired implantation position. With the template leg 204 in the desired implantation position, the guide frame 20 can be placed alongside the template leg 204 and adapted into the first mode of operation, as described above. It should be appreciated that if the tibia 215 requires anatomical reduction, such as in instances involving fracture, the reduction can be performed prior to or even after adapting the guide frame 20 into the first mode of operation.

Figure 9B:
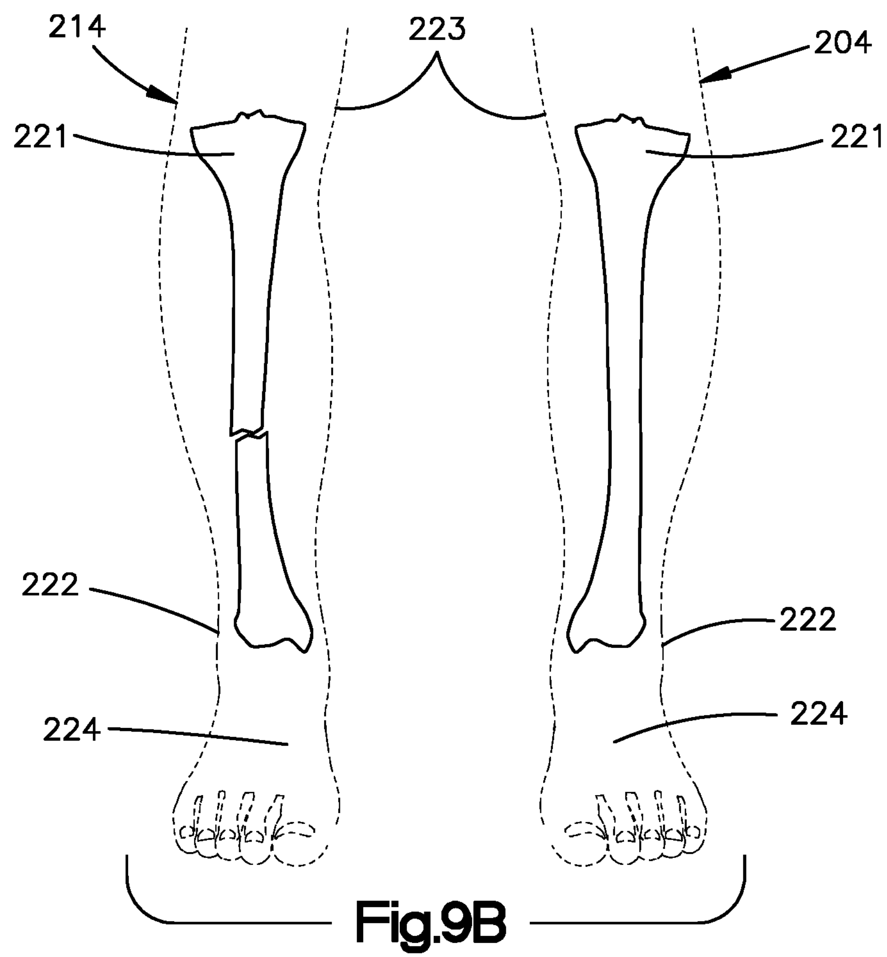
FIG. 9B is a diagrammatic view of a healthy limb and a contralateral injured limb of a patient.

To adapt the guide frame 20 into the first mode of operation, two or more and up to all of the reference members 26, 28, 30, 32 are placed into contact with their respective landmarks on the template leg 204. As shown in FIG. 9B, the first, second, third, and fourth landmarks, indicated by reference numerals 221, 222, 223, and 224, respectively, have contralateral positions on the template leg 204 and the implant leg 214. In the illustrated example, the first landmark 221 is the anterior-most point or apex of the proximal tibial head, the second landmark 222 is the lateral apex of the distal lateral malleolus of the fibula (i.e., the lateral apex of the ankle), the third landmark 223 is the lateral-most or medial-most portion of the knee, and the fourth landmark 224 is the top surface of the foot 209.

Figure 9C:
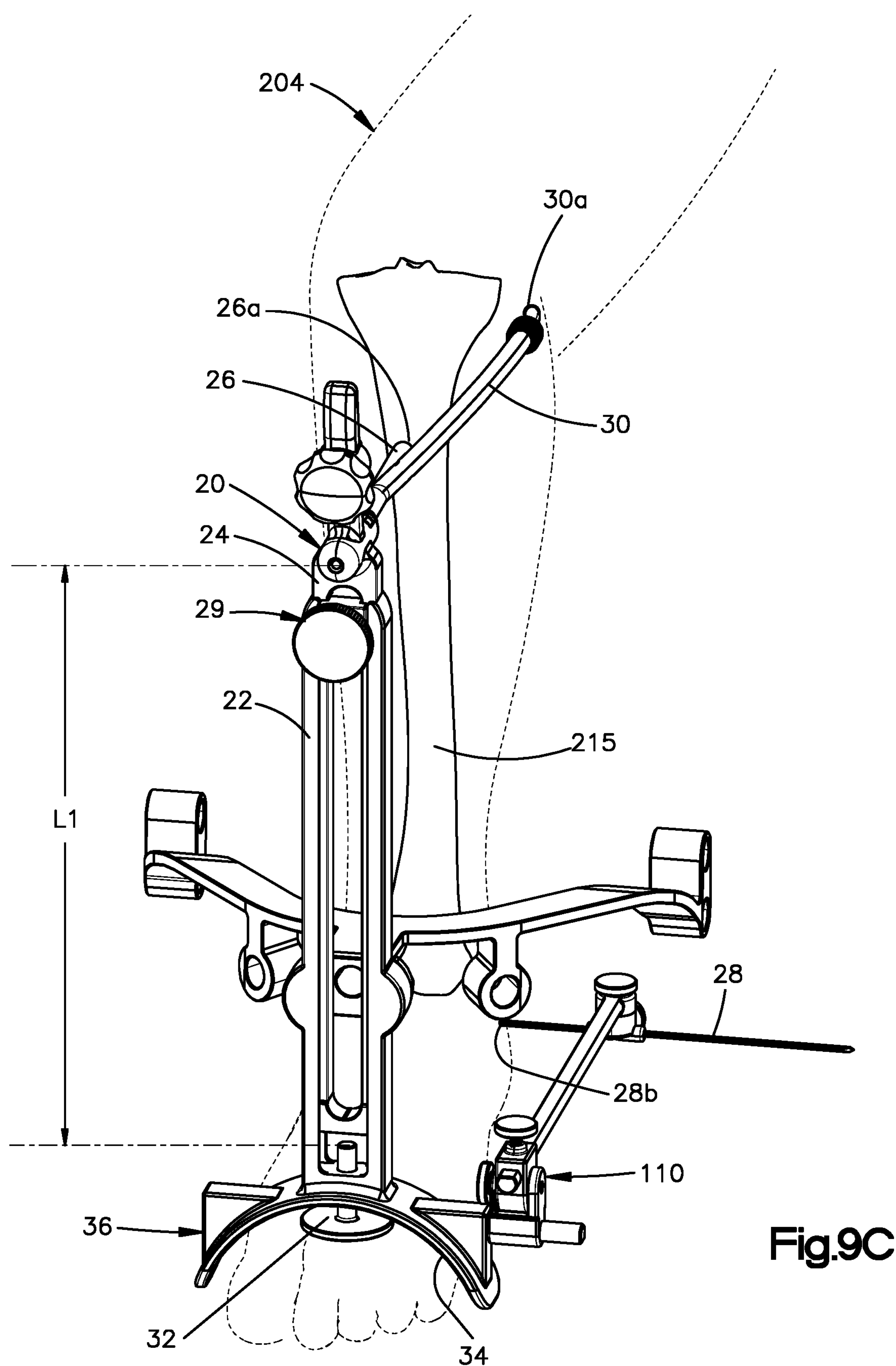
FIG. 9C is a perspective view of the aiming device of FIG. 1 adapted into a first mode of operation in which the aiming device is engaged with the healthy limb of the patient.

Referring now to FIG. 9C, adapting the guide frame 20 into the first mode of operation can include a step of determining the desired length L1 of the guide frame 20, which length L1 preferably also determines the length of the intramedullary nail 4 to be selected for implantation. Such a step can also be referred to as the "length-determining step," and can include: contacting at least one of the reference members 26, 30 extending from the adjustable member 24 against the respective landmark(s) 221, 223 on the template leg 204; iterating the primary position adjustment mechanism 29 between its locked and unlocked configurations, thereby allowing steps of translating the base and adjustable members 22, 24 longitudinally relative to each other to the desired length L1 and affixing the base and adjustable members 22, 24 together at the desired length L1; and contacting at least one of the reference members 28, 32 extending from the base member 22 against the respective landmark(s) 222, 224 on the template leg 204. For example, the length-determining step can include contacting the contact portion 26*a* of the first reference member 26 against the first landmark 221, such as the anterior-most point of the proximal tibial head, of the template leg 204. The length-determining step can also include moving the primary position adjustment mechanism 29 into its unlocked configuration (or, stated differently, "unlocking" the primary position adjustment mechanism 29), and translating at least one of the base and adjustable members 22, 24 relative to the other, and contacting the second reference member, such as the first end 28*b* thereof, against the second landmark 222 of the template leg 204, such as the lateral apex of the lateral malleolus of the ankle, for example.

It should be appreciated that placing the second reference member 28 into contact with the second landmark 222 can include adjusting the relative position between the second reference member 28 and the mounting formation 112 as needed using the positioning assembly 110, including any combination of the first, second, third, and fourth position adjustment mechanisms 140, 144, 152, 154 thereof (e.g., for translation along the arm direction 129, translation along direction 111, and rotation about pivot axis 146), and to thereafter lock the second reference member 28 into position. With the first and second reference members 28 in contact with their respective landmarks 221, 222, the length L1 can be set based on the physiological parameters of the template leg 204 (e.g., length) in the position in which it has been manipulated for implantation (e.g., flexion/extension of the lower leg 208 relative to the upper leg 210 about the knee 206).

It should be appreciated that the length L1 of the guide frame 20 should also be selected to be complimentary with the length L0 of the intramedullary nail 4 so that, when the nail 4 is implanted and the insertion handle 6 is mounted to the guide frame 20, the target axes 47, 49 of the drill guide

40 intersect the distal locking holes 14*b* of the nail 4. Thus, the length-determining step preferably includes using the visual indicia on the face 55 of the guide frame 20 to measure the resulting length L1 of the guide frame 20 and adjusting the length L1 as needed to be consistent with the length L0 of the intramedullary nail 4 for implantation (such as at least a select one of the intramedullary nails 4 in a kit having a plurality of nails 4). Using the visual indicia can include, for example, aligning the baseline arrows 68 with a pair of the hash marks 67 positioned at the regular length intervals, which correspond to the common length increments of the nails 4 in the kit. Accordingly, the length-determining step can include selecting the desired length L1 from between adjacent regular length intervals, which can require longitudinally translating the base and adjustable members 22, 24 relative to each other again until the baseline arrows 68 are aligned with a pair of the hash marks 67.

The length-determining step includes, after the length L1 has been adjusted as desired, moving the primary position adjustment mechanism 29 into its locked configuration (or, stated differently, "locking" the primary position adjustment mechanism 29), thereby affixing the length L1. If any additional translation prior to locking, such as to adjust the length L1 to one of the regular length intervals, moves the second reference member 28 out of contact with the second landmark 221, the positioning assembly 110 can be employed as needed to reposition the second reference member 28 into contact with the second landmark 221.

With the length L1 of the guide frame 20 determined, the physician can select from the kit the intramedullary nail 4 for implantation, particularly the nail 4 having length L0 that corresponds to length L1. It should be appreciated that the intramedullary nails 4 of the kit can be organized or otherwise categorized by their lengths L0. For example, the nails 4 can include a base nail that defines a minimum nail length L0 and additional nails 4 having respective lengths that differ from each other and from the minimum nail length L0 by multiples of a common length increment, such as 15.0 mm, by way of a non-limiting example. In such embodiments, the kit can include nails 4 having lengths L0 in a range from about 150 mm to about 500 mm, and more particularly in a range from about 200 mm to about 450 mm, and preferably in a range from about 250 mm to about 415 mm. The common length increment can be in a range from 1.0 mm to about 100 mm, and more particularly in a range from 5.0 mm to about 25.0 mm, and preferably in a range from about 10 mm to about 20 mm. It should be appreciated that the common length increment of the nails 4 in the kit is preferably equivalent to the regular length intervals of the visual indicia, such as the hash marks 67 on the face 55 of the base member 22. Furthermore, the step of selecting the intramedullary nail 4 for implantation can include referencing the number of multiples by which the length L0 of the selected intramedullary nail 4 differs from the minimum nail length. Thus, it can be said that the translating step involves adjusting the length L1 of the guide frame 20 substantially by the number of multiples of the common length increment of the nails 4 in the kit. In instances where the length L1 of the guide frame 20 is intermediate the regular length interval based on the landmarks of the template leg, the physician can preferably elect to reduce the length L1 to the closest shorter length interval, or alternatively (if circumstances permit), elect to increase the length L1 to the closes longer length interval.

The length-determining step can also include positioning the foot 209 of the template leg 204 within the receptacle 34, with can further include contacting the fourth contact portion 32*a* of the fourth reference member 32 against the fourth landmark 224 on the top surface of the foot 209. It should be appreciated that the longitudinal position of the fourth reference member 32 relative to the base member 22 can be adjusted as needed to provide precise corrections to the length L1 and/or the degree of flexion/extension of the foot 209 relative to the lower leg 208 during the length-determining step.

Adapting the guide frame 20 into the first mode of operation can also include contacting the third contact portion 30*a* of the third reference member 30 against the third landmark 223 of the template leg 204, such as the lateral-most or medial-most portion of the knee. The third landmark 223, in combination with the first and second landmarks 221, 222, can indicated the degree of flexion/extension of the template limb 204. It should be appreciated that the extension of the extendable body 98 relative to the anterior body 96 of the third reference member 30 can be adjusted as needed along axial direction 100 to contact the third landmark 223.

With at least one of the first and third reference members 26, 30 extending from the adjustable member 24 in contact with the respective first and third landmarks 221, 223 and at least one of the second and fourth reference members 28, 32 extending from the base member 22 in contact with the respective second and fourth landmarks 222, 224 and the length L1 of the guide frame 20 affixed, the guide frame 20 can be characterized as having been adapted to the template leg 204, thereby cumulatively defining or otherwise indicating the overall relative position between the template leg 204 and the guide frame 20. The guide frame 20 can then be disengaged from the template leg 204 and re-configured for contralateral use on the implant leg 214 in the second mode of operation.

It should be appreciated that, after adapting the guide frame 20 to the template leg 204 and prior to re-configuring the guide frame 20 for engagement with the implant leg 214 (i.e., between the first and second modes of operation), the physician can perform a step of verifying whether the target axes 47, 49 of the drill guide 40 intersect the distal locking holes 14*b* of the intramedullary nail 4 when the nail 4 is mounted to the adapted guide frame 20 (see FIG. 2). Such a verification step can include: coupling the nail 4 to the insertion handle 6; affixing the mounting structure 16 of the insertion handle 6 to the complimentary mounting structure 18 of the guide frame 20; and visually ascertaining whether the target axes 47, 49 of the drill guide 40 and guide sleeves 42 intersect the distal locking holes 14*b* of the nail 4. If the verifying step is performed between the first and second modes of operation, either the insertion handle 6 will be dismounted from the guide frame 20 or the intramedullary nail 4 will be uncoupled from the insertion handle 6 prior to the second mode of operation.

Figure 9D:
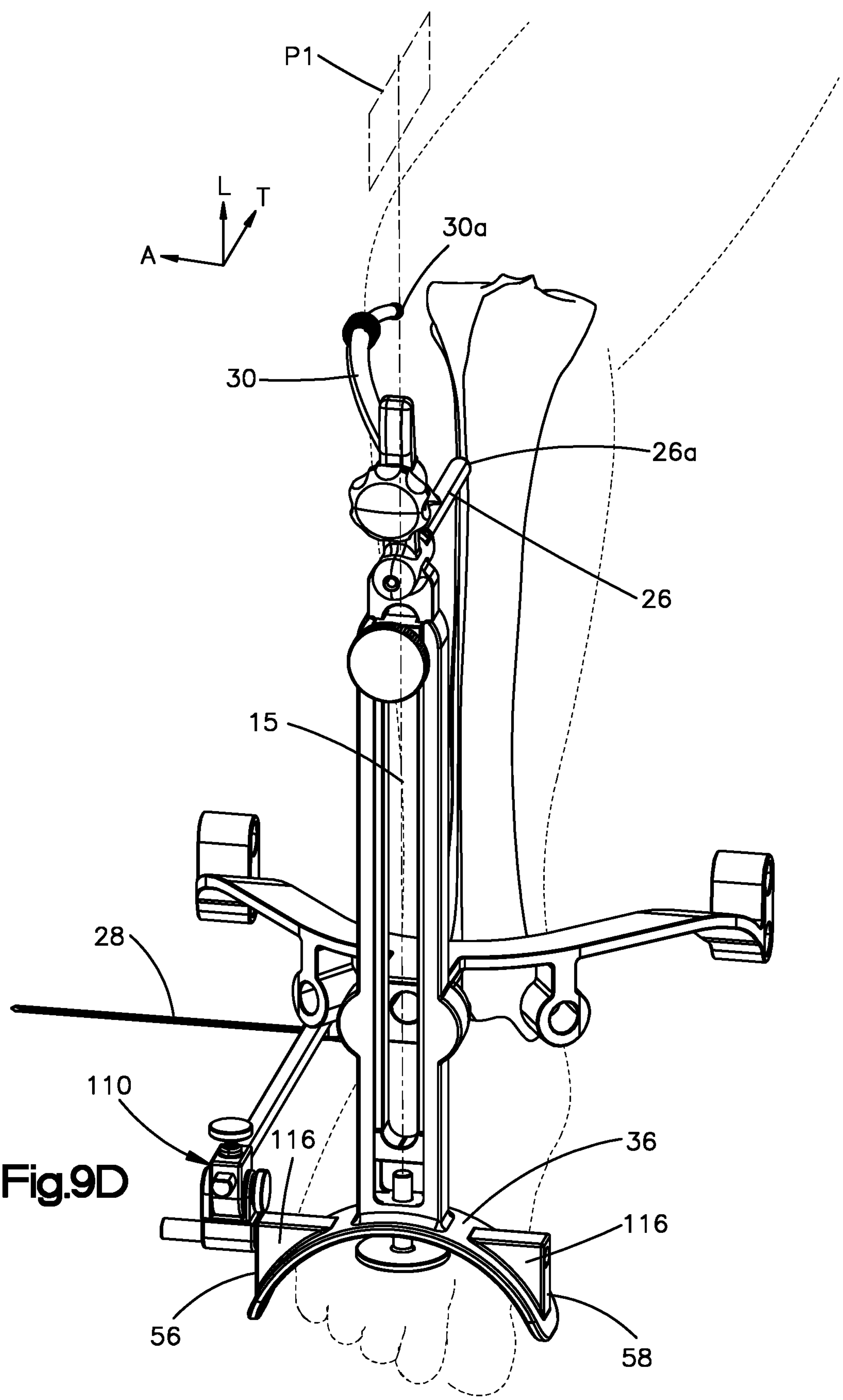
FIG. 9D is a perspective view of the aiming device of FIG. 1 re-configured into a second mode of operation in which the aiming device is engaged with the injured limb of the patient.

Referring now to FIG. 9D, in the second mode of operation, the physician re-configures the guide frame 20 for contralateral engagement with the implant leg 214, which assists in preparing the implant leg 214 to receive the nail 4. In particular, in the second mode of operation, the physician can use the re-configured guide frame 20 to assist manually manipulating the implant leg 214 into the position for implantation that was previously planned on the template leg 204. In this manner, the physician can use the guide frame 20 for replicating the physiological parameters (e.g., length, orientation and flexion/extension) of the template leg 204 onto the implant leg 214, to the extent possible or at least necessary for implantation, which also assists in subsequently aligning the distal locking holes 14*b* of the nail 4 with the target axes 47, 49 of the drill guide 40. Reconfigurating the guide frame 20 for contralateral symmetry can include repositioning the second reference member 28 on the base structure 36 symmetrically about the central reference plane P1 in the manner described above for contralateral symmetry, particularly by detaching the mounting structure 112 of the positioning assembly 110 from the receiving formation 116 on the respective side 56, 58 of the base structure 36 and attaching the mounting structure 112 to the other side 56, 58 of the receiving formation 116. If one of the ends 28*b*, c of the second reference member 28 is employed for contacting the second landmarks, the posterior carrier 132 can be pivoted 180 degrees about pivot axis 156, as described above. Additionally, the third reference member 30 can be pivoted about central axis 26*b* for contralateral symmetry in the second mode of operation.

With the second and third reference members 28, 30 repositioned for the second mode of operation, the physician can engage the guide frame 20 with the implant leg 214, which process can include contacting any and up to all of the first, second, third, and fourth landmarks 221, 222, 223, 224 of the implant leg 214 respectively against any and up to all of the first, second, third, and fourth reference members 26, 28, 30, 32. It is to be appreciated that any anatomical asymmetry between the template and implant limbs 204, 214 (such as those resulting from any injury or malady that caused the implant limb to require surgical repair, and/or those differences that may be naturally occurring or otherwise pre-existing to the injury or malady) should be considered when manipulating the implant leg 214 into contact with the any of the reference members 26, 28, 30, 32 for replicating the orientation and flexion/extension of the template leg 204.

With the implant leg 214 manipulated into a position for implantation with the assistance of the guide frame 20, the guide frame 20 can be temporarily disengaged from the implant leg 214, such as for mounting the intramedullary nail 4 to the guide frame 20 for performing another verification that the target axes 47, 49 of the drill guide 40 intersect the distal locking holes 14*b* when the nail 4 is mounted to the guide frame 20 (see FIG. 2). It should be appreciated that the drill guide 40 can be coupled with or decoupled from the guide frame 20 as needed during the first and second modes of operation.

Figure 9E:
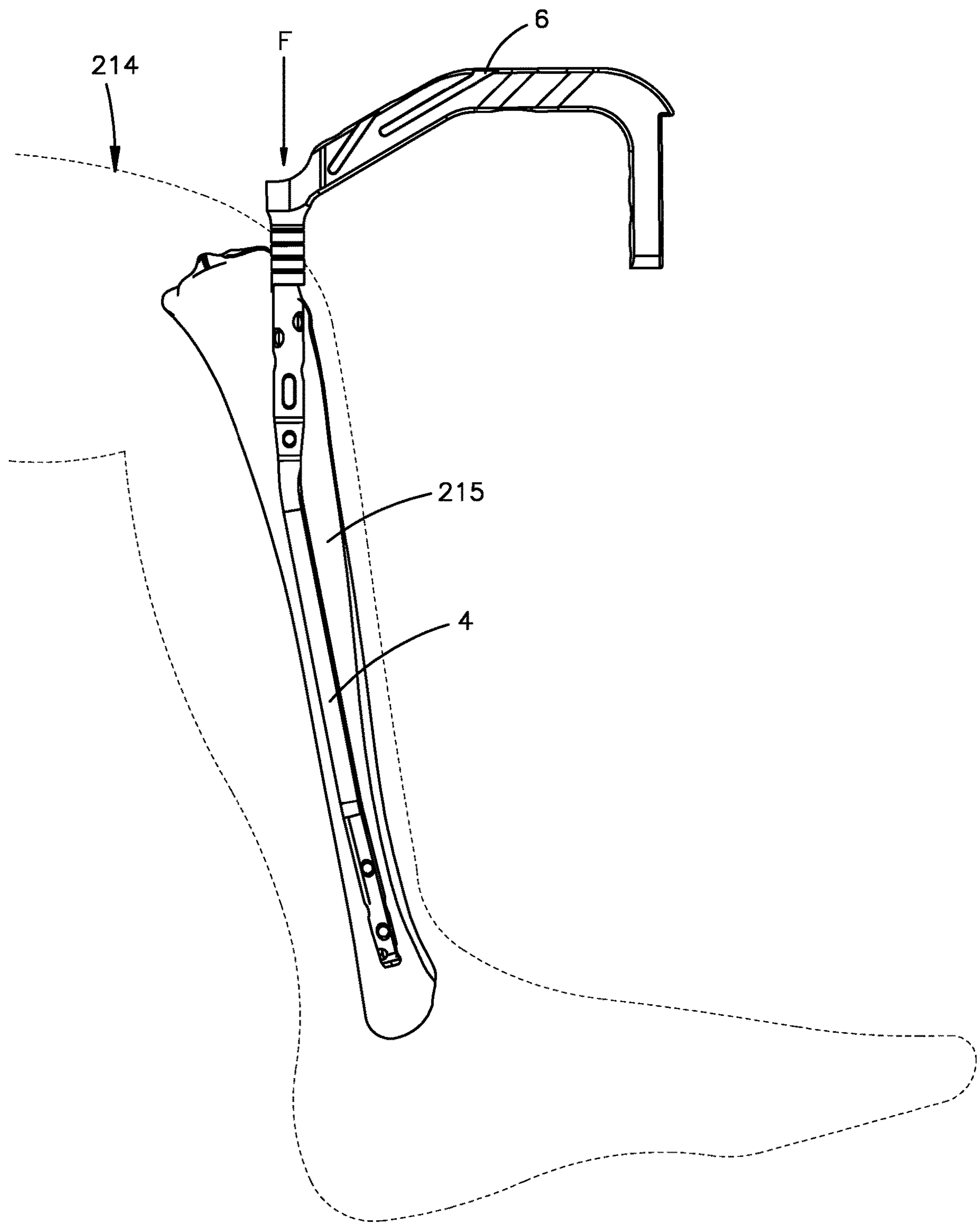
FIG. 9E is a side view of the intramedullary nail of the system illustrated in FIG. 9 inserted within the medullary canal of the tibia of the injured leg, according to an embodiment of the present disclosure.

Referring now to FIG. 9E, with the implant leg 214 prepared to receive the intramedullary nail 4, the physician can insert the nail 4 within the medullary canal of the tibia 215 of the implant leg 214. As shown, the intramedullary nail 4 is preferably mounted to the insertion handle 6 during the inserting step, such that the insertion handle 6 is employed to exert a driving force F on the nail 4 in a manner forcing the nail 4 into and along the medullary canal. As shown, the guide frame 20 can be disengaged and remote from the implant leg 214 during the insertion step. In other embodiments, however, the guide frame 20 can optionally remain engaged with the implant leg 214 during the inserting step, such as to maintain the desired position and orientation of the implant leg during the insertion procedure. In such instances, the guide frame 20 is preferably unattached to insertion handle 6 during the inserting step. The implantation procedure itself can include techniques known in the art, including: making an incision at a desired entry point adjacent the proximal head of the tibia 215, advancing a drill through the incision and drilling through the cortex of the tibia 215 and into the medullary canal, inserting a guide wire through the drill hole and into the medullary canal and optionally through the fracture site(s), reaming the drill hole and/or the medullary canal for receiving the nail 4, and inserting the nail 4 within the medullary canal, particularly by exerting the driving force F on the insertion handle 6 (such as by impacting the insertion handle with a mallet).

Figure 9F:
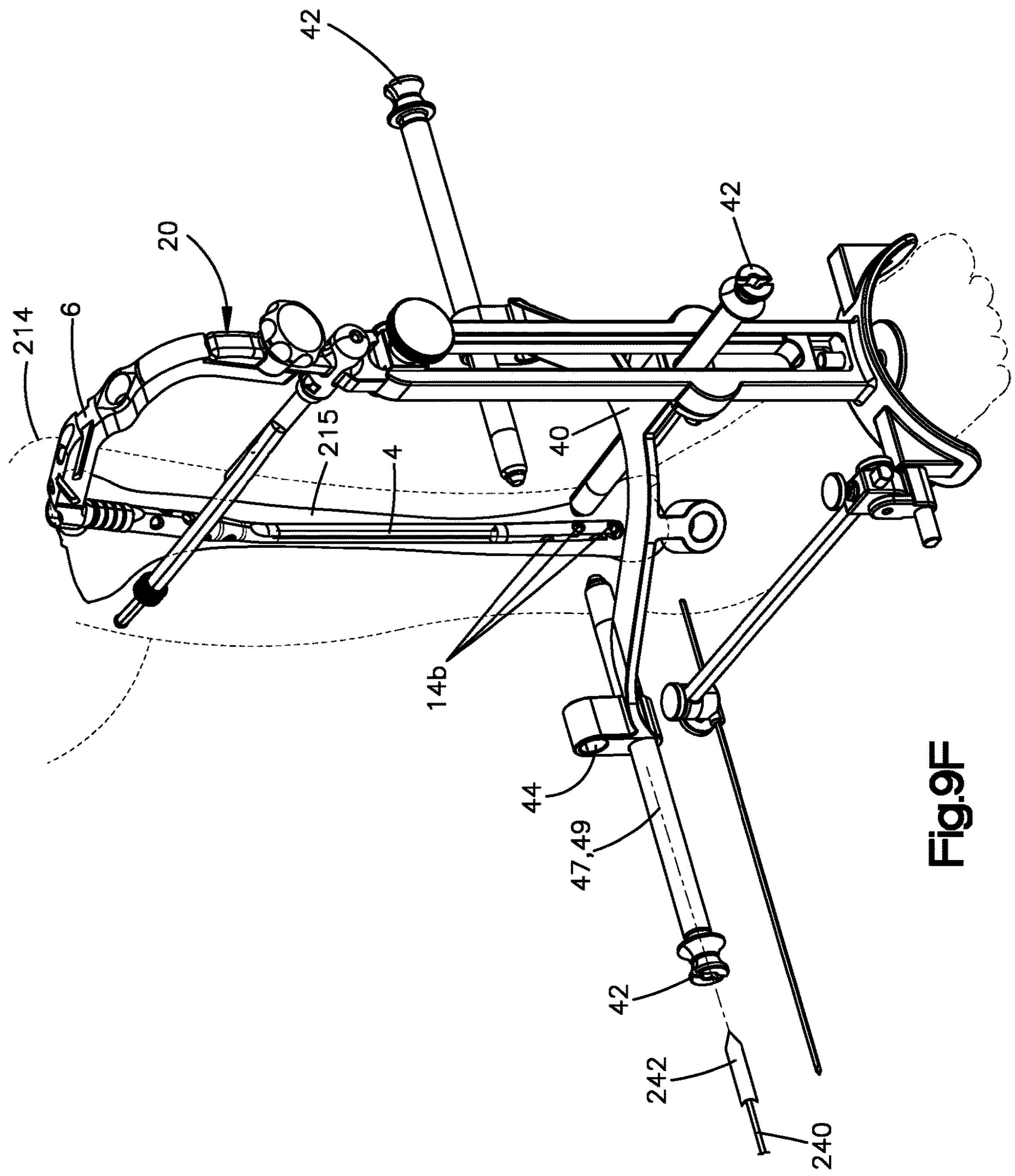
FIG. 9F is a perspective view of the implanted intramedullary nail further coupled to the aiming device illustrated in FIG. 9D for targeting the distal locking holes of the intramedullary nail, according to an embodiment of the present disclosure.

Referring now to FIG. 9F, after inserting the nail 4 in the medullary canal, the guide frame 20 is attached to the insertion handle 6 for locking the nail 4 within the medullary canal. The reference members 26, 28, 30, 32 can be checked to ensure that the nail 4 has been inserted into the planned position relative to the landmarks 221, 222, 223, 224 and, if needed, to assist the physician with final insertion adjustments to the nail 4 to the desired position. If the drill guide 40 had been decoupled from the guide frame 20 during any of the previous steps, the drill guide 40 will be re-coupled to the guide frame 20 for the step of locking the nail 4. With the drill guide 40 coupled to the guide frame 20 and the guide frame 20 attached to the handle member 6 extending from the inserted nail 4, the guide sleeves 42 can be inserted through the guide channels 44 of the drill guide 40, and can optionally be advanced along their axes 47 until distal ends of the sleeves 42 abut the exterior surface of the implant leg 214. As described above, the guide sleeves 42 can be employed for guiding movement of one or more instruments therethrough. For example, the locking step can include: advancing a scalpel or other instrument through the guide sleeve 42 and making a stab incision in the leg; subsequently advancing a drill bit through the sleeve 42, through the incision, through the near cortex of the tibia 215, and optionally through a corresponding one of the distal locking holes 14*b* and further optionally into and/or through the far cortex of the tibia 215; removing the drill bit and advancing a driver 240 carrying a locking member, such as a locking screw 242, through, in succession, the sleeve 42, the incision, the near cortex, and preferably through the targeted locking hole 14*b* and into and/or through the far cortex.

It should be appreciated that the sequence of one or more of the preceding steps can be adjusted as needed based on the particular needs of the patient and the resources available to the physician.

Figure 10:
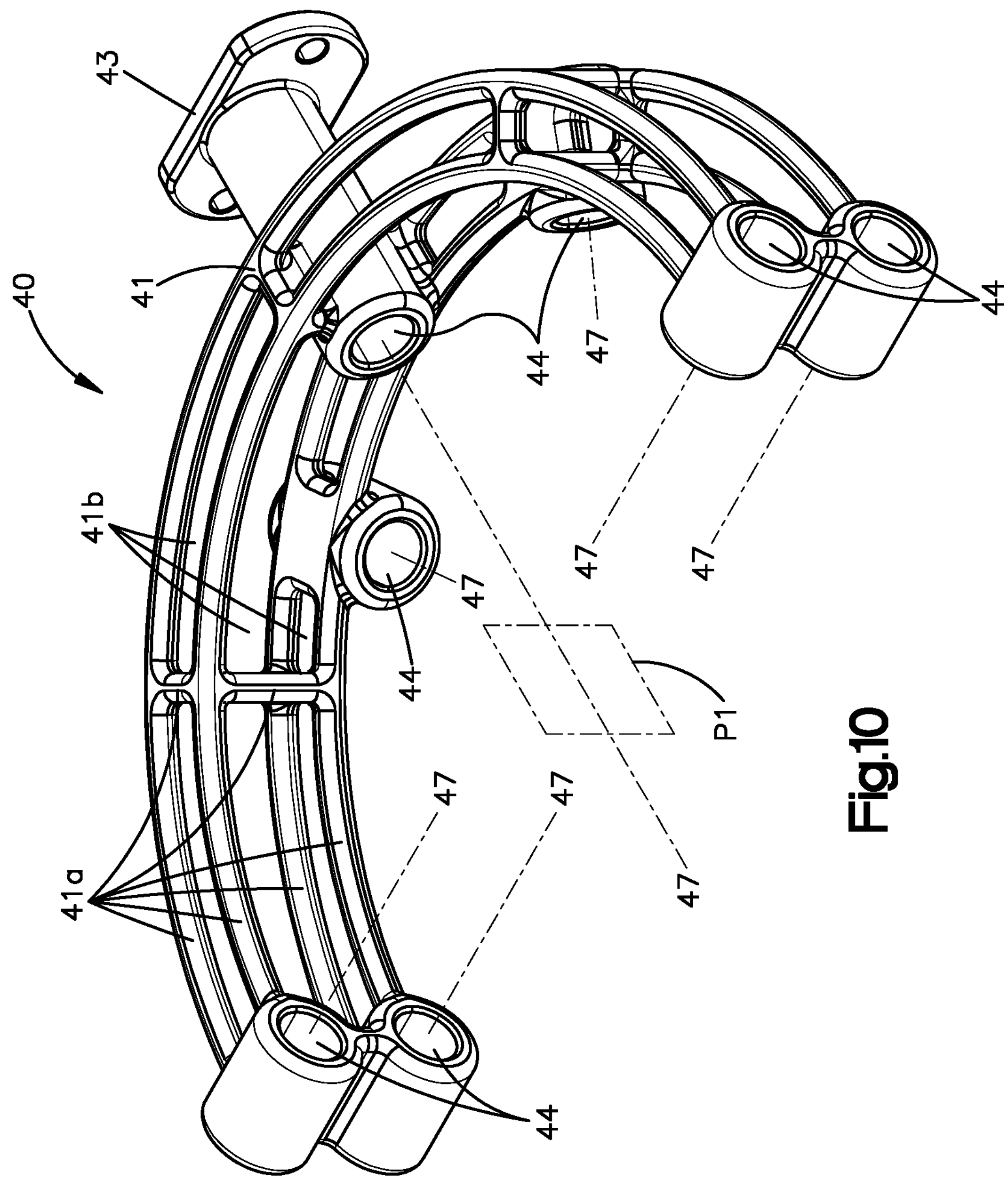
FIG. 10 is a perspective view of another embodiment of the targeting guide member illustrated in FIG. 1.

Referring now to FIG. 10, another embodiment of the drill guide 40 is shown for use with the aiming device 12 described herein. The drill guide body 41 of the present embodiment has a frame-like structure that includes a plurality of interconnected arms 41*a* defining a plurality of empty spaces 41*b* therebetween. Similarly as described above, the drill guide 40 of the present embodiment can include a mounting formation 43 configured to mount to the complimentary mounting structure 45 of the base member 22. Also, as above, the plurality of guide channels 44 can include a first subset of the guide channels 44 that are positioned on the first side of the central reference plane P1 and are positioned and oriented symmetrically about the central reference plane P1 from a second subset of the guide channels 44 on that are positioned on the second side of the central reference plane P1. The frame-like structure of the present embodiment can reduce the weight of the drill guide 40, and also provide increased visibility for the physician. Stated differently, the frame-like structure of the drill guide 40 provides less obstruction to the physician's view during use of the drill guide 40 for targeting the distal locking holes 14*b* of the intramedullary nail 4.

The inventors have discovered, through extensive testing, that the aiming device 12 of the present disclosure is significantly more effective at successfully targeting and inserting locking screws within the distal locking holes 14*b* of the implanted nail than other techniques that do not involve radiology and/or fluoroscopy.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A device for guiding implantation of an intramedullary nail, comprising:

a guide frame including a base frame member and an adjustable frame member coupled to the base frame member, wherein the adjustable frame member is configured to translate relative to the base frame member along a longitudinal direction;

an insertion handle configured to carry the intramedullary nail, the insertion handle configured to mount to the adjustable frame member;

a drill guide attachable to the base frame member, the drill guide configured to carry one or more guide sleeves for alignment with locking holes extending through the intramedullary nail;

a first reference member extending from one of the base frame member and the adjustable frame member, the first reference member having a first contact portion configured to contact a select exterior location of a limb of a patient; and a second reference member extending from the other of the base frame member and the adjustable frame member, the second reference member having a second contact portion configured to contact a second select exterior location of the limb, wherein at least one of the first and second reference members is configured such that a relative position between the respective contact portion and the base frame member or the adjustable frame member from which it extends is adjustable;

wherein the base frame member and the adjustable frame member are each elongate along a longitudinal axis oriented along the longitudinal direction, and the guide frame defines a central reference plane that extends along the longitudinal axis and a central axis of the intramedullary nail when the insertion handle carries the intramedullary nail and is mounted to the adjustable frame member;

wherein the drill guide defines guide channels configured to receive the one or more guide sleeves, wherein a first subset of the guide channels on a first side of the central reference plane are symmetrical with a second subset of the guide channels on a second side of the central reference plane;

wherein the base frame member has a first end and a second end spaced from the first end along the longitudinal direction, the base frame member has a base structure at the second end, and the base structure defines a receptacle configured to receive a foot of the patient;

wherein the base structure has a first side and a second side spaced from each other along a lateral direction that is perpendicular to the longitudinal direction and orthogonal to the central reference plane, and the second reference member is configured to be selectively mounted to 1) one of the first and second sides of the base structure in a first mode of operation, in which the device is engaged with the limb, the limb being a first limb, and 2) the other of the first and second sides of the base structure in a second mode of operation, in which the device is engaged with a second limb of the patient, wherein the first and second limbs have contralateral symmetry with each other; and wherein the base structure has a first receiving formation at the first side and a second receiving formation at the second side, and the second reference member is carried by a positioning assembly that comprises:

a mounting formation configured to mount to 1) one of the first and second receiving formations in the first mode of operation, and 2) the other of the first and second receiving formations in the second mode of operation;

an arm having an anterior end and a posterior end opposite the anterior end, the arm extending from the mounting formation along a third direction having at least a directional component along a transverse direction that is perpendicular to the longitudinal and lateral directions, wherein a relative position between the arm and the mounting formation is adjustable along the third direction; and a carrier attachable to the arm, the carrier spaced from the mounting formation along the third direction, the carrier configured to carry the second reference member such that the second reference member extends along a fourth direction having at least a directional component along the lateral direction, wherein the positioning assembly is configured such that, in the first mode of operation, the second contact portion is configured to contact the second select exterior location of the first limb, and in the second mode of operation, the second contact portion is configured to contact a second select exterior location of the second limb, wherein the second select exterior locations of the first and second limbs are substantial contralateral anatomical counterparts of each other.

2. The device of claim 1, further comprising a position adjustment mechanism connected to the base frame member and the adjustable frame member, wherein the position adjustment mechanism includes a clamp member configured to iterate between a locked configuration, in which the base frame member and the adjustable frame member are rigidly fixed to each other, and an unlocked configuration, wherein the adjustable frame member is translatable relative to the base frame member along the longitudinal direction.

3. The device of claim 2, wherein the base frame member defines a channel elongated along the longitudinal direction, the adjustable frame member is received within the channel, and the channel and the adjustable frame member have complimentary shapes configured to guide translation of the adjustable frame member along the longitudinal direction.

4. The device of claim 3, wherein:

the channel extends from a first channel end to a second channel end spaced from each other along the longitudinal direction;

the base frame member has a first translation stop member at the first channel end; and the device further comprises a second translation stop member extending within the channel and located adjacent the second channel end, wherein the second translation stop member is adjustable along the longitudinal direction to adjust a range of translation of the adjustable frame member relative to the base frame member along the longitudinal direction.

5. The device of claim 4, wherein the second translation stop member has a stop surface positioned within the channel and a contact surface positioned within the receptacle, wherein the stop surface defines a minimum of the range of translation, and the second translation stop member is configured to be adjusted along the longitudinal direction until the contact surface contacts a portion of the foot positioned in the receptacle.

6. The device of claim 1, wherein the positioning assembly further comprises first and second adjustment mechanisms each coupled to the mounting formation, the first adjustment mechanism is configured for adjusting the relative position between the arm and the mounting formation along the third direction, and the second adjustment mechanism comprises a pivot joint configured for adjusting the relative position between the arm and the mounting formation about a pivot axis oriented along the lateral direction.

7. The device of claim 6, wherein the positioning assembly further comprises: a third adjustment mechanism carried by the arm, wherein the third adjustment mechanism is configured for adjusting a relative position between the second reference member and the carrier along the fourth direction; and a fourth adjustment mechanism carried by the arm, wherein the fourth adjustment mechanism includes the carrier and is configured for adjusting the relative position between the second reference member and the arm about an additional pivot axis oriented along a fifth direction perpendicular to the third and fourth directions.

8. The device of claim 1, further comprising a third reference member extending from the adjustable frame member, the third reference member having a third contact portion, wherein the third reference member is rotatable about a pivot axis extending along the central reference plane such that, in the first mode of operation, the third contact portion is configured to contact a third select exterior location of the first limb, and in the second mode of operation, the third contact portion is configured to contact a third select exterior location of the second limb, wherein the third select exterior locations of the first and second limbs are substantial contralateral anatomical counterparts of each other.

9. The device of claim 8, wherein the third reference member is elongate along a central axis, the third reference member including:

a first body that extends from the first reference member along the central axis of the third reference member;

a second body coupled to the first body and movable relative to the first body along the central axis of the third reference member, wherein the third contact portion is defined by the second body, and the third select exterior locations of the first and second limbs are proximally spaced from the first select exterior locations thereof such that the first and third select exterior locations collectively indicate a degree of flexion or extension of a distal portion of each limb relative to a respective proximal portion of each limb about a joint intermediate the first and third select exterior locations; and a position adjustment mechanism that is configured to iterate between a locked configuration, in which the first and second bodies are rigidly fixed to each other, and an unlocked configuration, in which the second body is outwardly movable from the first body along the central axis of the third reference member.

* * * * *